United States Patent
Cox et al.

(10) Patent No.: US 7,403,814 B2
(45) Date of Patent: Jul. 22, 2008

(54) METHOD, APPARATUS, AND COMPUTER PROGRAM PRODUCT FOR ASSESSMENT OF ATTENTIONAL IMPAIRMENTS

(75) Inventors: Daniel J. Cox, Charlottesville, VA (US); Boris P. Kovatchev, Amherst, VA (US); Rayna S. Robeva, Amherst, VA (US); Jennifer Kim Penberthy, Manakin Sabot, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 758 days.

(21) Appl. No.: 10/476,826

(22) PCT Filed: May 6, 2002

(86) PCT No.: PCT/US02/14188

§ 371 (c)(1),
(2), (4) Date: Nov. 3, 2003

(87) PCT Pub. No.: WO02/091119

PCT Pub. Date: Nov. 14, 2002

(65) Prior Publication Data

US 2004/0152995 A1     Aug. 5, 2004

Related U.S. Application Data

(60) Provisional application No. 60/367,894, filed on Mar. 26, 2002, provisional application No. 60/360,295, filed on Feb. 27, 2002, provisional application No. 60/288,654, filed on May 4, 2001.

(51) Int. Cl.
A61B 5/04 (2006.01)

(52) U.S. Cl. .................................................. 600/544

(58) Field of Classification Search .................. 600/544, 600/545, 300
See application file for complete search history.

(56) References Cited

U.S. PATENT DOCUMENTS 4,421,122 A    12/1983 Duffy
4,846,190 A    7/1989 John (Continued)

OTHER PUBLICATIONS

Amen, D.G, et al., "High-Resolution Brain SPECT Imaging in ADHD," Annals of Clinical Psychiatry, vol. 9, No. 2, pp. 81-86, (1997).

(Continued)

Primary Examiner—Charles A. Marmor, II
Assistant Examiner—Navin Natnithithadha
(74) Attorney, Agent, or Firm—Novak Druce DeLuca + Quigg LLP; Robert J. Decker

(57) ABSTRACT

A method, apparatus, and computer useable medium that provides, among other things, a standardized test protocol for screening and evaluation of attentional impairment using EEG data. Further, the method, apparatus, and computer program product enhances existing psychological, behavioral, and physiological EEG data acquisition systems by introducing a sequential stochastic model procedure, and an intelligent data interpretation component capable of assessing EEG inconsistencies associated attentional impairments. Potential users of this product will be any person or organization that diagnoses or treats persons with attentional or cognitive impairments. The method can be used for initial screening and diagnosis of disorders associated with impaired attention, such as ADHD, as well as for treatment and evaluation of the effects of treatments, such as medication or additional therapies.

31 Claims, 13 Drawing Sheets

U.S. PATENT DOCUMENTS

| | | | |
|---|---|---|---|
| 4,913,160 A | | 4/1990 | John |
| 5,010,891 A | * | 4/1991 | Chamoun .................. 600/544 |
| 5,083,571 A | | 1/1992 | Prichep |
| 5,176,145 A | | 1/1993 | Ryback et al. |
| 5,287,859 A | | 2/1994 | John |
| 5,309,923 A | | 5/1994 | Leuchter et al. |
| 5,310,195 A | | 5/1994 | Abdallah |
| 5,320,109 A | * | 6/1994 | Chamoun et al. ........... 600/544 |
| 5,377,100 A | | 12/1994 | Pope et al. |
| 5,406,957 A | | 4/1995 | Tansey |
| 5,549,118 A | | 8/1996 | John et al. |
| 5,550,021 A | | 8/1996 | Blum et al. |
| 5,724,987 A | | 3/1998 | Gevens et al. |
| 5,913,310 A | | 6/1999 | Brown |
| 5,983,129 A | | 11/1999 | Cowan et al. |
| 6,044,292 A | | 3/2000 | Heyrend et al. |
| 6,097,980 A | | 8/2000 | Monastra et al. |
| 6,115,631 A | | 9/2000 | Heyrend et al. |
| 6,186,145 B1 | | 2/2001 | Brown |
| 6,210,950 B1 | | 4/2001 | Johnson et al. |
| 6,366,813 B1 | | 4/2002 | DiLorenzo |
| 6,434,419 B1 | * | 8/2002 | Gevins et al. ............... 600/544 |
| 6,549,804 B1 | * | 4/2003 | Osorio et al. ............... 600/544 |
| 6,746,409 B2 | | 6/2004 | Keirsbilck |
| 6,843,774 B2 | | 1/2005 | Foust et al. |
| 2003/0065535 A1 | | 4/2003 | Karlov et al. |

OTHER PUBLICATIONS

Biederman, J., et al., "Motor preference, major depression and psychosocial dysfunction among children with attention deficit hyperactivity disorder," J. of Psychiatric Research, vol. 28, No. 2, pp. 171-184, (1994).

Cox, D. J., et al., "Electronencephalographic and Psychometric Differences Between Boys With and Without Attention-Deficit/Hyperactivity Disorder (ADHD): A Pilot Study," Applied Psychophysiology and Biofeedback, vol. 23, No. 3, pp. 179-188., (1999).

Crawford, H., et al., "Quantitative EEG magnitudes in children with and without attention deficit disorder during neurological screening and cognitive tasks," Child Study Journal, vol. 26, No. 1, pp. 71-86, (1996).

Goyette, C. H., et al., "Normative Data on Revised Conners Parent and Teacher Rating Scales," J. of Abnormal Child Psychology, vol. 6, No. 2, pp. 221-236, (1978).

Merkel, R. L., et al., "The EEG Consistency Index as a Measure of Attention Deficit/Hyperactivity Disorder and Responsiveness to Medication: A Double blind Placebo Controlled Pilot study," Applied Psychophysiology and Biofeedback vol. 25, No. 3 pp. 133-142, (2000).

Schachar, R., et al., "Deficient inhibitory control in Attention Deficit Hyperactivity Disorder," J. of Abnormal Child Psychology, vol. 23, No. 4, pp. 411-437, (1995).

Tannock, R., et al., "Methylphenidate and cognitive flexibility: Dissociated dose effects in hyperactive children," J. of Abnormal Child Psychology, vol. 23, No. 2, pp. 235-266, (1995).

Vaidya, C. J., et al., "Selective effects of methylphenidate in attention deficit hyperactivity disorder: A functional mangetic resonance study," Proc. Natl. Acad. Sci. USA, vol. 95, 14494-14499, (1998).

Chabot, R. J., et al., "Quantitative Electroencephalographic Profiles of Children with Attention Deficit Disorder," Society of Biological Psychiatry, vol. 40, pp. 951-963, (1996).

Monastera, V. J., "Assessing Attention Deflicit Hyperactivity Disorder via Quantitative Electroencephalography: An Initial Validation Study," Neuropsychology, vol. 13, No. 3, pp. 424-433, (1999).

Ritchie, K., et al., "Classification criteria for mild cognitive impairment: A population-based validation study," Neurology, vol. 56, No. 1, pp. 37-42, (2001).

Ballard, C., et al., "Attention and Fluctuating Attention in Patients with Dementia with Lewy Bodies and Alzheimer Disease," Archives of Neurology, vol., 58, No. 6, pp. 977-982, (2001).

Grodstein, F., et al., "Type 2 Diabetes and Cognitive Function in Community-Dwelling Elderly Women," Diabetes Care, vol. 24, No. 6, pp. 1060-1065, (2001).

Sohlberg, M., et al., "Improving Attention and Managing Attentional Problems: Adapting Rehabilitation Techniques to Adults with ADD," Annals of New York Academy of Sciences, vol. 931, pp. 359-375, (2001).

Armstrong, C., et al., "Neurocognitive Problems in Attention Deficit Disorder: Alternative Concepts and Evidence for Impairment in Inhibition of Selective Attention," Annals of New York Academy of Sciences, vol. 931, pp. 196-215, (2001).

Meyer, J., et al., "Cardiovascular and Other Risk Factors for Alzheimer's Disease and Vascular Dementia," Annals of New York Academy of Sciences, vol. 903, pp. 411-423, (2000).

Chang, L., et al., "Neural correlates of attention and working memory deficits in HIV patients," Neurology, vol. 57, No. 6, pp. 1001-1007, (2001).

Pohjasvaara, T., et al., "Evaluation of Various Methods of Assessing Symptoms of Cognitive Impairment and Dementia," Alzheimer Disease and Associated Disorders, vol. 15, No. 4, pp. 184-193, (2001).

Doraiswamy, P. M., et al., "The Alzeheimer's Disease Assessment Scale: Evaluation fo Psychometric Properties and Patterns of Cognitive Decline in Multicenter Clinical Trials of Mild to Moderate Alzheimer's Disease," Alzheimer Disease and Associated Disorders, vol. 15, No. 4, pp. 174-183, (2001).

Goldman, L.S., et al., "Council Report of Diagnosis and Treatment of ttention-Deficit/Hyperactivity Disorder in Children and Adolescents," J. of the American Medical Association, vol. 279, pp. 1100-1107, (1998).

Clarke, A. R., , et al., "EEG analysis in attention-deficit/hyperactivity disorder: A comparative study of two subtypes," Psychiatry Research, vol. 81, pp. 19-29, (1998).

McDonald, S., "Covert orienting and focusing of attentioin in children with attentiion deficit hyperactivity disorder," Neuropsychologia, vol. 37, No. 3, pp. 345-356, (1999).

Kovatchev, B.P., "A Psychophysiological Marker of Attention Deficit/Hyperactivity Disorder (ADHD) Defining the EEG Consistency Index," Applied Psychophysiology and Biofeedback, vol. 26, No. 2, (2001).

* cited by examiner

FIG. 10: Stochastic Transition: Linking Sequential Assessment Steps

FIG. 11: Diagnostic Assessment

FIG. 12: Assessment of Treatment Effectiveness

METHOD, APPARATUS, AND COMPUTER PROGRAM PRODUCT FOR ASSESSMENT OF ATTENTIONAL IMPAIRMENTS

CROSS-REFERENCES TO RELATED APPLICATIONS

The present invention is a national stage filing of International Application No. PCT/PCT/US02/14188, filed 6 May 2002, which claims benefit under 35 U.S.C. Section 119(e) from U.S. Provisional Patent Application Ser. No. 60/288,654 filed May 4, 2001, entitled "The Consistency Index—An EEG Marker of Attention Deficit Hyperactivity Disorder," 60/360,295 filed Feb. 27, 2002, entitled "Method and Apparatus for Assessment of Attentional Impairments: A Psycho-Physiological Procedure," and 60/367,894 filed on Mar. 26, 2002, entitled "Method and Apparatus for Assessment of Attentional Impairments: A Psycho-Physiological Procedure," the entire disclosures of which are hereby incorporated by reference herein in their entirety.

FIELD OF THE INVENTION

The present invention relates to the assessment of individuals with attentional impairments, and more particularly an apparatus and method for using electroencephalographic (EEG) data for making various types of assessments pertaining to various types of attentional impairments.

BACKGROUND OF THE INVENTION

Impairments in cognitive ability and attention are pervasive and potentially debilitating components of many disorders, conditions, injuries and diseases, including mild cognitive impairment (MCI) in persons with pre-dementia, dementia, dementia with Lewy bodies, Alzheimer's Disease, traumatic brain injury, Attention Deficit/Hyperactivity Disorder (ADHD), and cognitive/attentional declines associated with chronic diseases such as diabetes, cardiovascular disease, and HIV infection [1, 2, 3, 4, 5, 6, 7, 8]. Most of these disorders are assumed to be pathology-based and therefore amenable to intervention, especially if diagnosed early. Despite the staggering number of such conditions, the significance of such cognitive and attentional impairments in these conditions, and the importance of early, accurate, and comprehensive assessment and diagnosis, there is currently no such procedure or set of standards to employ to quantify such impairments, either when diagnosing the disorder or examining effectiveness of treatment.

For example, the recent NIH Consensus Statement on Attention Deficit/Hyperactivity Disorder [9] concluded that ADHD is difficult to diagnose, considered a common problem, and is associated with many negative consequences, both for the patient and society, and has been inconsistently associated with neuroimaging and EEG anomalies that have been non-diagnostic in nature.

ADHD is one of multiple disorders associated with impairments in attention. Although this document may particularly identify attentional disorders associated with ADHD, the present invention shall be applied to any disorder with associated attentional impairments. With respect to dementia, recent research and a review of the literature conclude that the frequency of post stroke dementia and cognitive decline varied sharply when different systems of diagnostic classification and methods were used [10]. Furthermore, recent findings support the need for validation not only of the criteria, but also the need for validated measures to diagnosis dementia and cognitive impairment post stroke [10, 11, 12], and Alzheimer's disease [13]. In addition, cognitive abnormalities commonly occur in patients with HIV infection [14]. Among otherwise healthy HIV-positive patients, cognitive deficits are thought to be infrequent [15], but some investigators suggest that more sensitive measures may be needed to detect the mild cognitive decline during the asymptomatic stage [16].

Diagnostic Dilemma

There are numerous disorders and diseases associated with impairment of attention and cognitive functioning, however, the diagnosis and quantification of impairment of attention in any disease or disorder is typically difficult. Some examples include: attentional impairments associated with ADHD, HIV infection, Alzheimer's Disease, cardiovascular disease, diabetes, and dementia.

With respect to ADHD, the DSM-IV [17] states "The essential features of ADHD is a persistent pattern of inattention and/or hyperactivity-impulsivity that is more frequent and severe than is typically observed in individuals in a comparable level of development." Evidence of six of nine inattentive behaviors and/or six of nine hyperactive-impulsive behaviors must have been present before age seven, and must clearly interfere with social, academic and/or occupational functioning. Consequently, the diagnosis of ADHD is highly dependent on a retrospective report of a patient's past behavior and subjective judgements on degree of relative impairment. Due to the subjective nature of assessment, precision in diagnosis has been elusive. ADHD is complex and influences all aspects of a person's life. It can co-exist with and/or mimic a variety of health, emotional, learning, cognitive, and language problems. An appropriate, comprehensive evaluation for ADHD includes a medical, educational, and behavioral history, evidence of normal vision and hearing, recognition of systemic illness, and a developmental survey. The diagnosis of ADHD should never be made based exclusively on rating scales, questionnaires, or tests [18].

Prevalence

Since ADHD cannot be strictly defined, and precisely and objectively measured, its true prevalence cannot be accurately determined. While the DSM-IV estimates the prevalence of ADHD in school-age children as between three percent and five percent, other community survey studies suggest it may be as high as 16 percent [19]. ADHD occurs more commonly in males than in females, with ratios ranging from 4:1 to 9:1. Of all child referrals for mental health services, one-third to one-half is thought to be attributable to ADHD.

According to recent projections [20], Alzheimer's disease will affect increasing numbers of people as baby boomers (persons born between 1946 and 1964) age. The annual number of incident cases is expected to more than double by the midpoint of the twenty-first century: from 377,000 in 1995 to 959,000 in 2050. The proportion of new onset cases that are age 85 or older will increase from forty percent in 1995 to 62 percent in 2050.

It is clear from the number of persons suffering from attentional or cognitive difficulties or deficits, that there is a need for accurate diagnosis and validation of treatment efficacy. It is also clear that the portion of the population who will be suffering from cognitive decline or impairment will continue to increase with the overall aging of the population and the increased diagnosis of attentional disorders. There is therefore a need in the art for a comprehensive, flexible, and an effective diagnostic measure of attentional abilities.

Negative Consequences

The hallmarks of ADHD are hyperactivity, impulsivity, and an inability to sustain attention. The DSM-IV distinguishes three types: predominantly inattentive type, predominantly hyperactive-impulsive type, and combined type. In addition to the core clinical symptoms of ADHD, high levels of co-morbidity have been found with learning, oppositional defiant, conduct, mood, and anxiety disorders. Furthermore, it is estimated that the majority of children diagnosed with ADHD exhibit significant behavioral problems during adolescence and manifest continuing functional deficits and psychopathology into adulthood. One real-life consequence of ADHD is a five-fold increase in automobile crashes [21].

Early diagnosis and treatment of Alzheimer's disease, dementia, and additional progressive disorders associated with attentional impairment is especially important because patients with early stages of dementia may show reversal of their cognitive deficits and neurochemistry abnormalities after treatment [8].

Neuroimaging and EEG Findings Related to ADHD

In spite of these well-documented problems, the mechanisms and etiology of ADHD remain methodologically difficult to study, with different studies yielding inconsistent results. Most investigators accept that ADHD exists as a distinct clinical syndrome and suggest a multifactorial etiology that includes neurobiology as an important factor. Zametkin and Rapoport [22] identified eleven separate neuroanatomical hypotheses that have been proposed for the etiology of ADHD. Most studies have concluded that either delayed maturation or defects in cortical activation play large roles in the pathophysiology of ADHD. For example, studies of cerebral blood flow determined by single-positron emission computerized tomography have demonstrated decreased metabolic activity in suspected attentional areas of the brain [23]. These, as well as additional neurophysiological findings, have been interpreted as evidence of delayed maturation and cortical hypoarousal in regions of the prefrontal and frontal cortex, the two predominate etiological theories underlying ADHD. Unfortunately, while neuroanatomical findings lend support to the notion that ADHD is a distinct clinical syndrome and add to our understanding of the etiology of ADHD, neuroimaging techniques are too expensive, restricted to a few centers, and lack clear specificity and sensitivity in diagnosis of ADHD. There is therefore a need in the art for an inexpensive and clear system and method for diagnosis of ADHS and other impairments.

There are a few basic methods of analyzing EEG data that have been employed in previous research—visual inspection of raw data and quantitative analyses of EEG data, including spectral and coherence methods of analysis. To date, none of these methods have revealed pervasive or consistent patterns of EEG abnormalities with sufficient specificity or sensitivity to separate children with ADHD from normal subjects. The first of these methods of analysis involves visual inspection of raw EEG data. As long ago as 1938, Jasper, Solomon, and Bradley, used this method and reported EEG abnormalities in children with minimal brain dysfunction (an outdated term used to describe children with hyperactivity and poor attentiveness as well as learning disabilities and conduct disorder). In parallel with the development of the computer, researchers have applied a second method of EEG analysis employing quantitative techniques. Quantitative EEG is a mathematical analysis of voltage-time series data with the intention of extracting useful information not readily apparent to visual inspection. Spectral analysis is a common technique of quantitative EEG. It mathematically transforms, via Fast Fourier Transform (FFT), raw amplitude-time data into its component frequencies. During the 1970s several laboratories utilized a combination of visual inspection and quantitative techniques, and reported differences between the EEGs of hyperactive and normal children. Among the differences discovered were: a higher percentage of abnormal EEG patterns (abnormal usually meaning excessive slow wave activity) in clinical subjects than in controls; more power in the 0 to 8 Hz spectrum in hyperactive children compared to normal controls; less power in the 10 Hz range for hyperactives than controls; and less beta and weaker stimulus-locked alpha attenuation in hyperactive than in non-hyperactive children. These early studies were typically confounded by inconsistent and often inadequate assessment procedures and methodologies. It is therefore not surprising that early research demonstrated no pervasive or consistent patterns of EEG data to discriminate hyperactive, inattentive, or impulsive children from controls.

Noticeably absent in the literature of that time, however, was information concerning extensive EEG frequency components obtained from several groups of clinical and control children engaged in tasks manipulating attention. Numerous investigators have reported that only when subjects are engaged in behavioral paradigms (particularly those manipulating attention) do electrophysiological differences appear between normal and hyperactive or LD children. Partially in response to this deficit in the research literature, Dykman et al. [24] investigated the EEGs of four groups of boys (10 hyperactive, 10 learning-disabled, 10 with both hyperactivity and LD) engaged in a complex visual search task. Spectral analysis of EEG data indicated that LD boys, hyperactive boys, and boys with a mixed diagnosis displayed less beta and less stimulus-locked alpha attenuation than normal boys. Thus, research in the 1980s-1990s began to address and correct issues of uniformity of diagnosis, methodology, and accuracy in EEG acquisition, both in terms of theoretical understanding and technical application. In an attempt to clarify some of the EEG differences between hyperactive and normal subjects, Satterfield, Schell, Backs & Hidaka [25] considered the impact of age upon EEG in two groups of normal (n=60) and hyperactive, inattentive, and impulsive males (n=138) ages 6-12, by examining follow-up EEGs on a subset of the hyperactive and normal subjects four years after the initial EEG. Their findings indicate that EEG power spectral intensities of normal male children decrease with increasing age. However, EEG power declines slower with increasing age in hyperactive subjects. Overall, instead of clarifying the issues, Satterfield et al. conclude that ". . . electrophysiological differences between hyperactive and normal male children are complex and vary markedly with age." They further warn that "Computation of group averages which include data from children of a wide age range may obscure rather than clarify the electrophysiological correlates of this disorder."

More recent studies employing spectral analysis of EEG have also shown varying patterns of EEG activity in ADHD subjects. Mann, et al. [26] tested 25 nine to twelve year-old boys with predominantly inattentive-type ADHD, and found increased theta at both absolute and relative percent power calculations, and decreased beta in temporal and frontal sites. Janzen et al. [27] compared EEG differences between eight ADD males and eight normal control males ages 9-12. Results demonstrated that the ADD males had higher theta amplitudes for all sites. However, unlike Mann et al., Janzen et al. found no differences between groups for beta-all amplitudes. Clarke et al. [28] performed automated EEG on subjects (ages 8-12) classified into groups of 20 ADHD-Combined Type, 20 ADHD-Predominantly Inattentive Type, and 20 controls. Overall, they found evidence of increased absolute and relative theta in all ADHD subjects, with the ADHD combined type showing a significantly greater amount of theta power than the predominantly inattentive-type. In addition, Clarke et al. found a decrease in alpha activity, but elevated theta present in all brain regions measured and not confined to frontal regions as previous studies had reported. In contrast to Mann, et al. they report less posterior absolute beta power in posterior regions. In an interesting study by Ackerman, et al. [29] a group of 56 ADD/ADHD children who had normal reading skills were employed as a control group, and their EEGs compared to EEGs of 119 children with reading disorders (some of whom had a co-morbid diagnosis of ADD/ADHD). Subjects included 86 males and 33 females between the ages of 7.5 and 12 years. Coherence analysis of EEG data is an additional method of quantitative analysis employed in a smaller number of studies, with equally inconclusive findings. Coherence analysis involves a cross-correlation that measures the relationship of activity at one site of the brain to another. In one of the largest studies procured to date, Chabot and Serfontein [30] tested 407 children with attention deficits with and without hyperactivity, with and without learning problems, children with attention problems who failed to reach DSM-III criteria for the disorder, and 310 controls (ages 6-17). They first employed spectral analysis and observed patterns of excess theta in frontal regions and increased alpha (relative power) in the posterior regions for the clinical groups versus controls. They then employed coherence analysis and reported that one-third of the non-control children showed signs of interhemispheric dysregulation characterized by this pattern of excessive theta/alpha power in the right temporal and premotor (frontal) areas.

Overall, although numerous studies have examined ADHD versus non-ADHD children using EEG, techniques in study design vary widely. Of the studies above, sixty percent involve only male subjects, eight of eleven studies used electrode caps for EEG acquisition, and only three employed a clinical control group in addition to a normal control group. Only seven of the studies specifically evaluate EEGs of diagnosed ADHD children (versus children displaying attentional deficits and no hyperactivity). Of these studies, five did report increased theta wave activity. However, these findings were not consistently found to involve similar brain regions (two in frontal region, one parietal region, one anterior region, and one all sites). Two of the seven studies reported decreased alpha wave activity, while two reported increased alpha relative power, and the remaining three reported no significant alpha wave findings. Again, of the seven studies involving ADHD diagnosed subjects, one reported decreased absolute beta in the posterior regions, one reported decreased relative beta in the posterior regions, one reported decreased beta in the right frontal region, two reported increased beta wave activity, and two reported no significant beta findings. The presence of theta and the absence of beta may be the neural substrate of the inability to shift between tasks in order to focus on the task at hand. This is affirmed in recent papers that hypothesize that an ADHD individual has difficulty in responding to the target task, not difficulty with ignoring peripheral stimuli [31]. Overall, the differences in EEG spectra between affected and unaffected children remain inconsistent and nonspecific enough to prevent their use as a diagnostic tool. In fact, in their 1993 review, Goldstein and Ingersoll [38] concluded that consistent differences in EEG have not been documented between those with and without ADHD.

There is therefore a need in the art for a method and apparatus for assessing attentional impairments of persons. The present invention provides a method for evaluating and quantifying comprehensive data from persons with attentional disorders. This data includes EEG information when transitioning from one cognitive task to another, behavioral information, cognitive performance, and history of symptoms. The data is examined within a sequential stochastic procedure, and used to diagnosis attentional disorders and evaluate treatment response.

BRIEF SUMMARY OF INVENTION

The present invention relates to the assessment of individuals with various attentional impairments, and assessing the treatment thereof, using EEG data.

In particular, a first aspect of the present invention is directed to a method, apparatus, and computer useable medium for assessing individuals for disorders associated with attentional impairments. The related method comprising (a) placing at least one electrode at a respective cranial site on an individual, (b) obtaining digitized EEG data at epochs of a plurality of frequency bands, the EEG data being collected from a first cognitive task period, a rest period, and a second cognitive task period (wherein the individual performs predetermined tasks during the first and second cognitive task periods, and the individual rests during the rest period, (c) processing the EEG data to determine electrophysical power (pW) obtained from the first cognitive task period and the second cognitive task period, (d) calculating the power change distance (PCD) between the first and second cognitive task periods, (e) filtering the PCD data by comparing the PCD data with a noise threshold number, (f) applying a cutoff frequency dividing the filtered PCD data into two ranges, a first range being PCD data below the cut-off frequency and a second range being PCD data above the cut-off frequency, (g) calculating a Consistency Index wherein the Consistency Index is defined by the absolute value of the difference between a sum of the below cut-off PCD data and a sum of the above cut off PCD data, and (h) comparing the Consistency Index to a control group database to provide the assessment of the individual.

Another aspect of the present invention is directed to a method, apparatus, and computer useable medium for assessing individuals for disorders associated with attentional impairments of the individuals. The related method comprising (a) placing at least one electrode at a respective cranial site on an individual, (b) obtaining digitized EEG data at epochs of alpha frequency, the EEG data collected from at least one sequence of a first cognitive task period, a rest period, and a second cognitive task period (wherein the individual performs predetermined tasks during the first and second cognitive task periods, and the individual rests during the rest period), (c) processing the EEG data to determine electrophysical power (pW) for a sequence of alpha powers ($\alpha_1, \alpha_2, \ldots \alpha_k$) obtained from at least one of the first cognitive task period, the reset period, and the second cognitive task period, (d) calculating an Alpha Blockade Index (ABI) for the determined alpha powers ($\alpha_1, \alpha_2, \ldots \alpha_k$), and (e) comparing the ABI to a control group database to provide the assessment of individual.

An additional aspect of the present invention is directed to a method, apparatus, and computer useable medium for assessing individuals for disorders associated with attentional impairments of the individuals. The related method comprising (a) assigning an individual a probability of attentional impairment for demographic assessment, (b) assigning an individual a probability of attentional impairment for psychometric assessment, (c) assigning an individual a probability of attentional impairment for Consistency Index, (d) assigning an individual a probability of attentional impairment for Alpha Blockade Index (ABI), (e) calculating conditional probabilities of assigned attentional impairment for at least one of steps (a) through (d), whereby the calculated conditional probability account for an assigned probability of an alternative step, and wherein the conditional probabilities provide an overall probability or range of probability for the individual, and (f) comparing the overall conditional probability or range of conditional probability to a control group database to provide the assessment of the individual.

In yet another aspect of the present invention, there is provided a method, apparatus, and computer useable medium for assessing the treatment that individuals receive for disorders associated with attentional impairments of the individuals. The related method comprising (a) assigning an individual a probability of attentional impairment for Consistency Index (b) assigning an individual a probability of attentional impairment for Alpha Blockade Index (ABI), (c) calculating conditional probabilities of assigned attentional impairment for at least one of steps (a) through (b), whereby the calculated conditional probability account for an assigned probability of an alternative step, and wherein the conditional probabilities provide an overall probability or range of probability for the individual; and (d) repeat steps (a) through (c) a desired number of times over a select duration to compare the success or efficacy of treatment.

These four aspects of the invention can be integrated together to provide a comprehensive, flexible, and effective diagnostic measure.

These and other objects, along with advantages and features of the invention disclosed herein, will be made more apparent from the description, drawings and claims that follow.

BRIEF SUMMARY OF THE DRAWINGS

The foregoing and other objects, features, and advantages of the present invention, as well as the invention itself, will be more fully understood from the following description of preferred embodiments, when read together with the accompanying drawings, in which:

FIGS. 2(A)-1(B) are graphical representations of the mean differences of the power spectra from task-to-task as recorded in FIGS. 1(A)-1(B).

DETAILED DESCRIPTION OF THE INVENTION

Consistency Index

Figure 1:
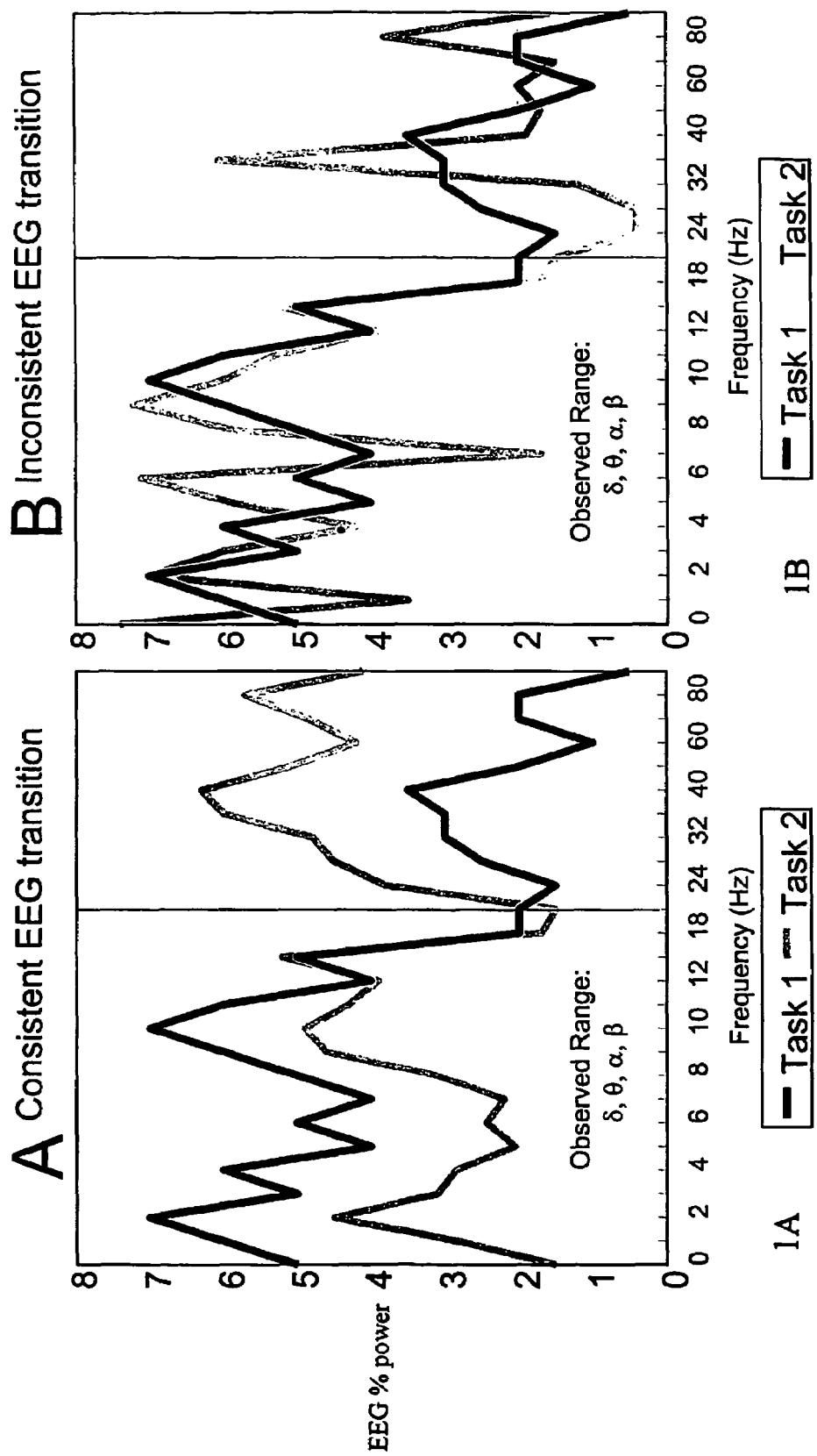
FIGS. 1(A)-1(B) are graphical representations of the EEG frequency dimension, illustrating the EEG power spectrum for two cognitive tasks for a consistent EEG transition case and an inconsistent EEG transition case, respectively.

The present invention is based on research conducted by the inventors that focused on ADHD in children and the EEG Consistency Index (CI)—a measure based on subjects' EEG shift when going from one cognitive task to another. Cumulatively, the inventors' studies demonstrated that: i) the CI discriminates, with almost no overlap, ADHD male subjects from controls; ii) the CI correlates significantly with psychometric measures of ADHD, and iii) the CI is reliable over time and is positively influenced by Ritalin. The inventors have introduced the Consistency Index as a new measure of EEG alterations related to ADHD and in several studies showed that, on the same data, it works better than the previously known measures. One reason for that is that the Consistency Index is computed on EEG differences between two tasks, and therefore cancels out "noise" inherent in the EEG measurement. The Consistency Index is a measure based on a mathematical model of EEG changes during transitions from one cognitive task to another. The hallmark component of attentional disorders is the inability to shift or transition between tasks (McDonald, et al., 1999) [32]. The CI is the first defined EEG diagnostic marker of attentional disorders and provides a new tool for assessment of ADHD, and additional disorders characterized by impairment of attention.

The original CI ("CI 1") is measured while subjects perform multiple alternating cognitive tasks (10-35 minutes) such as watching videos or reading, with rest periods with eyes open (5 minutes) in between.

A first aspect of the present invention provides inter alia the enhancement of diagnostic accuracy of the EEG CI by employing a second version of the Consistency Index ("CI2"), and furthermore this new measure ("CI2") can add significantly to the EEG classification of individuals with ADHD, especially for boys under the age of 16. Specifically, findings to date indicate that a form of the Consistency Index using the sum of the absolute differences (labeled CI2 to differentiate it from the original CI), consistently differentiated controls from ADHD subjects, with a high specificity (only 3 out of 20 controls misclassified) and provided good sensitivity (only 3 out of 16 ADHD subjects misclassified). The CI2 is calculated from the same data obtained during the procedure defined for the CI1. The inventors have accumulated data for over 150 ADHD/non-ADHD subjects which provides an improved perspective of the problems so as to arrive at the following conclusions (and unless otherwise stated, the CI discussed hereafter shall be considered the CI2 subject matter):

(1) Attentional deficits influence EEG records in a different way at different levels of resolution in terms of time. More precisely: power of Theta and Engagement Index are measured on a temporal scale of the order of milliseconds; Consistency Index is measured on a time scale of the order of 10 minutes. At this time there is no assessment of EEG alterations measured in any intermediate scale. Also proposed is that a rapid succession of approximately 1-minute cognitive tasks successfully differentiates adults with attentional deficits from adults without attention deficits. The rapid succession technique shall be discussed later in this document as a second aspect of the present invention.

(2) Any one of the existing measures is not powerful enough to make a clear distinction between individuals with and without attentional deficits (with the Consistency Index being currently the best). However, a carefully weighted combination of several measures in the form of a sequential stochastic model would work best for assessment of cognitive and attentional disorders. The sequential stochastic model shall be discussed later in the document as a third aspect of the present invention.

With the increase in specificity and sensitivity related to incorporating the CI2 (first aspect of the present invention) with the CI1, the ability of the rapid succession of 1-minute cognitive tasks to successfully differentiate adults with attentional deficits from adults without attention deficits (second aspect of the present invention), and the incorporation of additional disorder specific psychometrics and ratings to provide the sequential stochastic procedure (third aspect of the present invention), the present invention can be utilized as an accurate and comprehensive assessment tool to diagnose and quantify change in attentional and cognitive impairment.

Regarding the first aspect of the present invention, in a preferred embodiment the procedure uses standard EEG equipment and a standard electrode cap with electrode placement according to the standard 10-20 system. Example of EEG type systems are illustrated in Monastra, et al. U.S. Pat. No. 6,097,980; Heyrend et al. U.S. Pat. No. 6,044,292, John et al., U.S. Pat. No. 5,549,118; Tansey, U.S. Pat. No. 5,406,957; and John, U.S. Pat. No. 5,287,859; and are hereby incorporated by reference herein in their entirety. The technician needs to demonstrate first that the impedance of all electrodes is below 5 k ohms. Then, the data acquisition protocol for computing the Consistency Index (CI) comprises a subject reviewing a video for approximately ten minutes. This will involve the subject selecting from a library of age appropriate videotapes a film of their choice to view for twenty minutes. The data from the first ten minutes will be considered adaptation period and will be discarded. Next, the subject takes about a five-minute break. This can be a brief unstructured break and electrode resistance check. Subjects are asked to keep their eyes open and remain still. Thereafter, the subject may take about a ten-minute reading test. The reading portion of the test will involve the subject silently reading for about ten continuous minutes from a book of their choice that is within their reading ability level.

The present invention model is based on the concept that the EEG data stream can be represented by a three-dimensional numeric array (at any given moment one dimension is frequency of brain waves), another is spatial (the location of the electrode on a subject's head), and the third is time. ADHD can cause inconsistency in the frequency or spatial dimension or in both when shifting across cognitive tasks.

The present invention EEG assessment procedure begins with a standard EEG data acquisition/transformation sequence: The raw EEG data are digitized amplitudes sampled about 200 times a second through scalp electrodes. A Fast Fourier transformation (FFT) is used to compute the power spectrum of the data, epoch by epoch. One skilled in the art would appreciate that various modes for computing the transform may be employed besides the FFT depending of factors such ass the type of signal be analyzed, the available processing capability, etc. For example, but not limited thereto, the invention may employ the Fourier Transform (FT), Short-Time FT (STFT), Discrete Cosine Transforms (DCT), or wavelet transforms (WT). The frequencies represented in this spectrum are, depending on the filter settings, between 0.5-2 and 80-100 Hz. This region includes four basic EEG frequency bands: Delta (0.5-4 Hz), Theta (4-8 Hz), Alpha (8-13 Hz) and Beta (13-22 Hz). Separately recorded (and generally not included in further analysis) is High Beta+ EMG (22-40 Hz) and the residual power, carried by frequencies above 40 Hz. This picture is scanned by a number of EEG electrodes at different locations of a subject's head. The basic CI uses only 8 electrodes, F3, F4, CZ, PZ, C3, C4, P3, P4, however the present invention model is flexible enough to accommodate experiments with other locations, such as FZ, F7, F8, P7, P8, T7, T8. The FFT is updated epoch by epoch at one-second increments. Thus, during testing each person gets a three-dimensional (frequency-location-time) power spectrum representation.

Using a series of figures depicting the sequential steps of the computation of the CI, the present invention shall be discussed further.

FIGS. 1(A)-1(B) are graphical representations of the EEG frequency dimension, illustrating the EEG power spectrum for two cognitive tasks for a consistent EEG transition case and an inconsistent EEG transition case, respectively. These graphs present the basis of the concept of a consistent EEG in the frequency dimension. The black line is the power spectrum of a subject performing a task; the gray line is the power spectrum of the same subject while performing an adjacent task. In FIG. 1(A) the black line is above the gray line at lower frequencies and mostly below the gray line at higher frequencies (above 16 Hz). This shows that a shift from one task to another (from black to gray) results in an increase of higher frequencies and a decrease of lower frequencies. In contrast, in FIG. 1(B) no specific change in the frequency distribution over is observed.

The term "consistent" is best defined by looking at mean differences of power spectra from task-to-task (See FIG. 2(A)). As shown in FIG. 2(A), this difference is mostly positive at lower frequencies and mostly negative at higher frequencies. As shown in FIG. 2(B), the power differences are scattered below and above the frequency axis. Visually, a consistent shift between two tasks will be presented by an uninterrupted domain (FIG. 2(A)) while an inconsistent shift would result in sporadic power changes along the EEG spectrum, as in FIG. 2(B).

FIGS. 3(A)-3(B) are graphical representations of the EEG spatial dimension for the various location of the electrodes. As opposed to the frequency dimension, the presentation of spatial EEG consistency is based on a discrete presentation of the power spectrum at several EEG channels. FIGS. 3(A)-3(B) presents an 8-channel (electrode) setting and spatially consistent/inconsistent shifts between two tasks. The continuous spectrum at each electrode is integrated into (four in this example) frequency bands. A consistent shift would mean that at a particular frequency band at most channels will display similar, unidirectional readings (FIG. 3(A)), while an inconsistent shift will result in scattered power changes across the electrode sites (FIG. 3(B)). An alternative embodiment will use 21-channel EEG system, which changes the data retrieval software, but not the general idea of spatial EEG consistency. It would be appreciated that any quantity of channels may be utilized.

Figure 2:
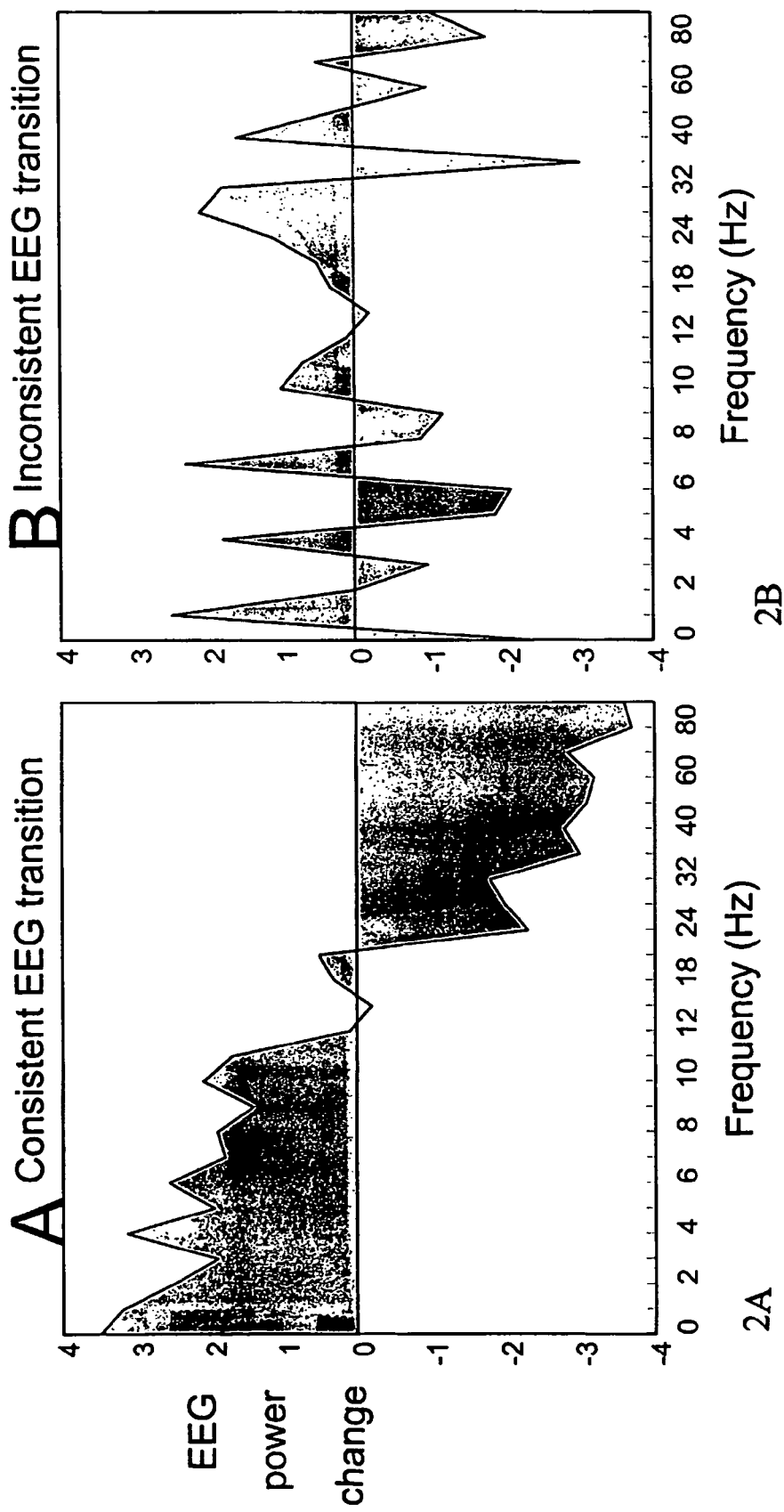
Figure 3:
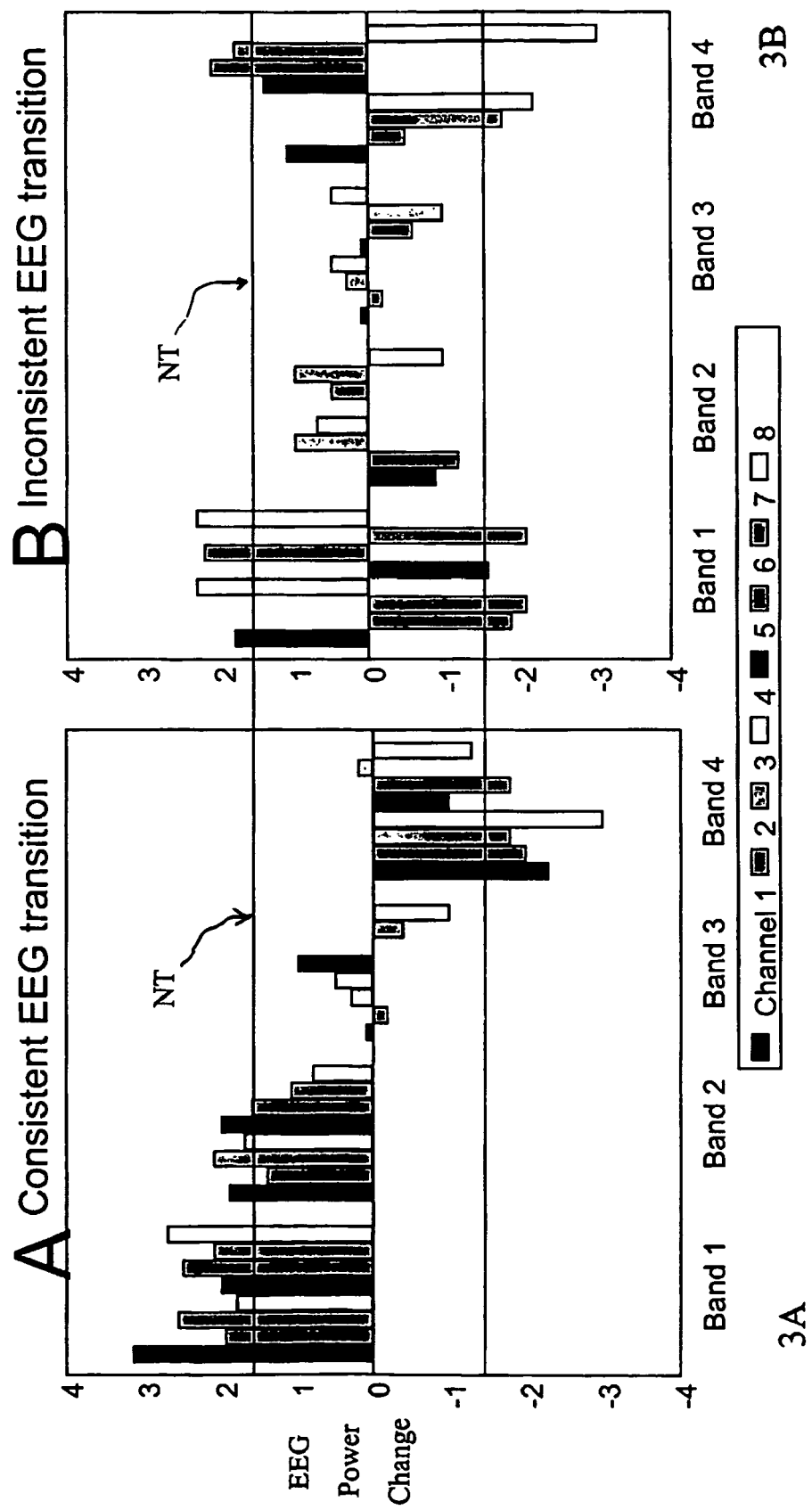
FIGS. 3(A)-3(B) are graphical representations of the EEG spatial dimension for the various location of the electrodes for a consistent EEG transition case and an inconsistent EEG transition case, respectively.

The EEG consistency, as shown FIGS. 1-3, is used as a basis for the development of the present invention related algorithm and software that computes the CI. In a preferred embodiment the algorithm works as follows.

1) Discrete spectra, including residual power, are calculated for all EEG channels through a standard EFT algorithm;

2) Power change distances (PCD) between two contiguous tasks are computed for each EEG band and channel according to equation no. 1.

$$PCD = \frac{M1 - M2}{\sqrt{\frac{SD_1^2}{N1} + \frac{SD_2^2}{N2}}} \quad (1)$$

Initially, each PCD is normalized using the formula of equation no. 1, where M1 and M2 are the mean powers at two contiguous tasks, SD1 and SD2 are their standard deviation, and N1 and N2 are the epoch counts at these tasks. Normalization allows changes in one channel/frequency band to be directly comparable to another;

3) PCD undergo filtering to eliminate changes below a "noise threshold." The noise threshold, presented by horizontal lines in FIGS. 3(A)-3(B), works as follows: The PCD that are larger by an absolute value than the threshold will be marked with 1 or −1 depending on their direction, while all PCD below threshold will be marked by zero. In FIGS. 3(A)-3(B) noise thresholds of ±1.65 are presented by the line designated as NT. These thresholds transform the PCD of FIGS. 3(A)-3(B) into a sequence of 1, 0, −1 that indicates, for each EEG band and channel, whether a significant power change was observed while the person shifted from one task to another. Since the PCD have a distribution close to Student t-distribution, a threshold of 1.65 is equivalent to making an one-tailed t-test comparing the average EEG power at Task 1 and 2 at p=0.05. Once again, this is just an association provided to clarify our methods. No conclusions based on t-test or any other parametric technique are involved in the computation of the CI. The noise threshold value is adjustable and for an alternative embodiment the noise threshold is 3.5.

Figure 4:
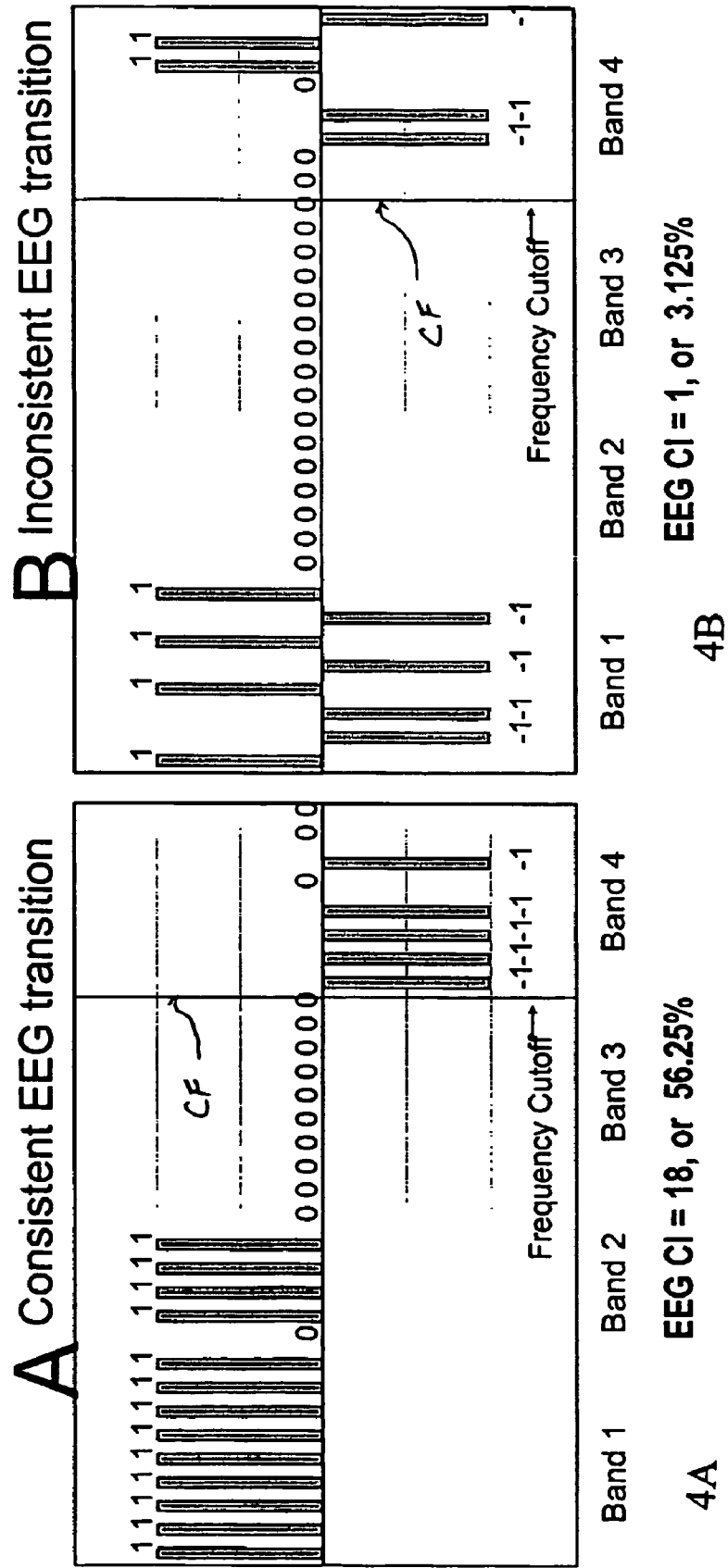
FIGS. 4(A)-(B) are the graphical representations of the filtered set of PCD for a consistent EEG transition case and an inconsistent EEG transition case, respectively.

4) The filtered set of PCD is presented in FIGS. 4(A)-(B). The shift from task one to task two would be consistent if most of the filtered PCD below some cutoff frequency are positive, while most of the indicators above this cutoff frequency are negative, or vice versa. In contrast, the shift would be inconsistent if the PCD vary greatly by magnitude and/or sign. Thus, FIGS. 4(A)-(B) present a consistent and an inconsistent EEG, respectively, at a cutoff frequency between beta and high beta, as denoted by the line CF.

5) The final pass of the computation is an addition of the filtered PCD below and above the cutoff value. The CI is defined as the absolute value of the difference between these two sums, expressed as a percentage, i.e., computed using equation no. 2 below:.

$$CI = 100 \left| \frac{1}{N} \left( \sum_{belowcutoff} \delta_i - \sum_{abovecutoff} \delta_j \right) \right| \% \text{ where } \delta_i, \delta_j = -1, 0, 1 \quad (2)$$

For example, in FIG. 4(A) there is provided a sum of 13 below the cutoff and a sum of −5 above the cutoff. Thus, the CI of the consistent shift presented in FIG. 4(A) will be 18. In contrast the CI of the inconsistent shift in FIG. 4(B) will be 1 (0 below the cutoff and −1 above the cutoff). The maximum CI equals the number of EEG channels multiplied by the number of EEG bands used during spectrum discretization. For example, with 8-channel EEG equipment and 4 bands the CI ranges from 0 to 32. In order to make the results comparable across different experiments, the CI will be expressed in terms of percentage from its maximum value. For example, the CI in FIG. 4(A) will be 56.25 percent, while in FIG. 4(B) it will be 3.125 percent.

An alternative embodiment of the CI can be computed as the sum of absolute values of the PCD. This version has properties similar to the CI and in some studies has shown superior discrimination ability.

Alpha Blockage Index

A second aspect of the present invention shall provide a method, apparatus, and computer program product for providing intermediate temporal scale readings monitored in the form of training to decrease alpha blockade during the rapid succession of approximately 1-minute cognitive tasks. Such a method may be used for neurofeedback to implement improved attentional abilities.

With respect to monitoring alpha blockade and providing neurofeedback, in traditional EEG, activities of the waking EEG in alpha frequencies have special significance in that they form the "alpha rhythm," a posteriorly-dominant activity that attenuates (or "blocks") with eye opening. This rhythm first emerges at age 3-4 month and gradually increases in frequency until adult levels are attained in late childhood. Since the alpha rhythm is slowed or absent during heightened anxiety or extremely low arousal such as drowsiness, attaining alpha enhancement (increasing power of alpha) is more difficult for both over-aroused subjects (such as ADHD subjects) and for under-aroused subjects (again, such as ADHD subjects or other persons suffering from inattention). Control subjects have demonstrated a significant difference in the power of alpha, with a higher power during rest and a lower power of alpha during cognitive tasks. Since alpha enhancement results from reduction of alpha blocking influences, on-line neurofeedback of the power of alpha can be presented to the subject with attention difficulties, with the instructions to facilitate relaxation when at rest. Instructions to concentrate when shifting to the cognitive task can also be used to facilitate alpha blocking, thus inversely increasing the power of beta, associated with mental concentration and focus.

Similarly, neuropsychological EEG studies have attributed certain changes in powers of frequency band under specific testing conditions. The presence of beta activity is considered by most psychophysiologists to reflect active mental processing, whereas alpha is associated with relaxation and delta and theta with underarousal. The attenuation of alpha and theta activity and the presence of beta activity signify "active mental processing" in these paradigms [33]. Therefore, neurofeedback in the intermediate scale of a few minutes will be provided regarding increasing alpha during rest periods and suppressing alpha when engaged in cognitive tasks.

Regarding the Alpha Blockade Index (ABI) EEG data acquisition procedure, the raw EEG data are digitized amplitudes sampled about 200 times a second through scalp electrodes and FFT is used to compute the power spectrum of the data, epoch by epoch. The power of Alpha frequencies (8-13 Hz) is computed for all epoch and then averaged within every task and rest period and across the EEG electrodes. Thus, for each person there is obtained a sequence of alpha powers $\alpha_1$, $\alpha_2, \ldots \alpha_k$, corresponding to the sequence of rapidly changing tasks and rest periods.

In particular, the subjects will engage in a cognitive task for about 1-2 minutes requiring concentrated cognitive effort, (e.g. tracking on a computer screen). Next, the subjects are then asked to take a break for about 1 minute, while they keep their eyes open and remain still. Thereafter, the subjects resume their cognitive tasks stated above for about 1-2 minutes. This series may then be repeated comprising alternating tasks and breaks for up to about 12 trials (approximately one hour) or other desired level of repetition.

The ABI may also be calculated as a step in the sequential stochastic model (to be discussed later as a third aspect of the present invention). Such ABI data will also provide on-line feedback approximately every one to two minutes indicating the power of alpha during task and rest. The objective will be for the subjects to increase their power of alpha during rest and minimize the power of alpha while performing the cognitive tasks.

The ABI for a person during the rapid transition protocol is computed as follows:

$$ABI = \frac{100}{k-1} \cdot \sum_{i=2}^{k} \left| \frac{\alpha_i - \alpha_{i-1}}{\max(\alpha_{i-1}, \alpha_i)} \right| \quad (3)$$

Similarly to the CI, AI ranges from 0 to 100 and, as the inventors data show, a lower AI is a sign of ADHD.

The CI and ABI result from a complex mathematical model and their computation is not straightforward. No standard statistical procedures can be applied to compute the CI, or ABI, and clearly they cannot be calculated manually. In a preferred embodiment, the present software is written in Java and has the following features: i) interface for reading data from 4- 8- and 21-channel EEG equipment, ii) capability of computing for any combination of threshold and cut-off parameters, and iii) processing of a list of subjects, and combining their indices into a suitable data base for further analysis.

Figure 13:
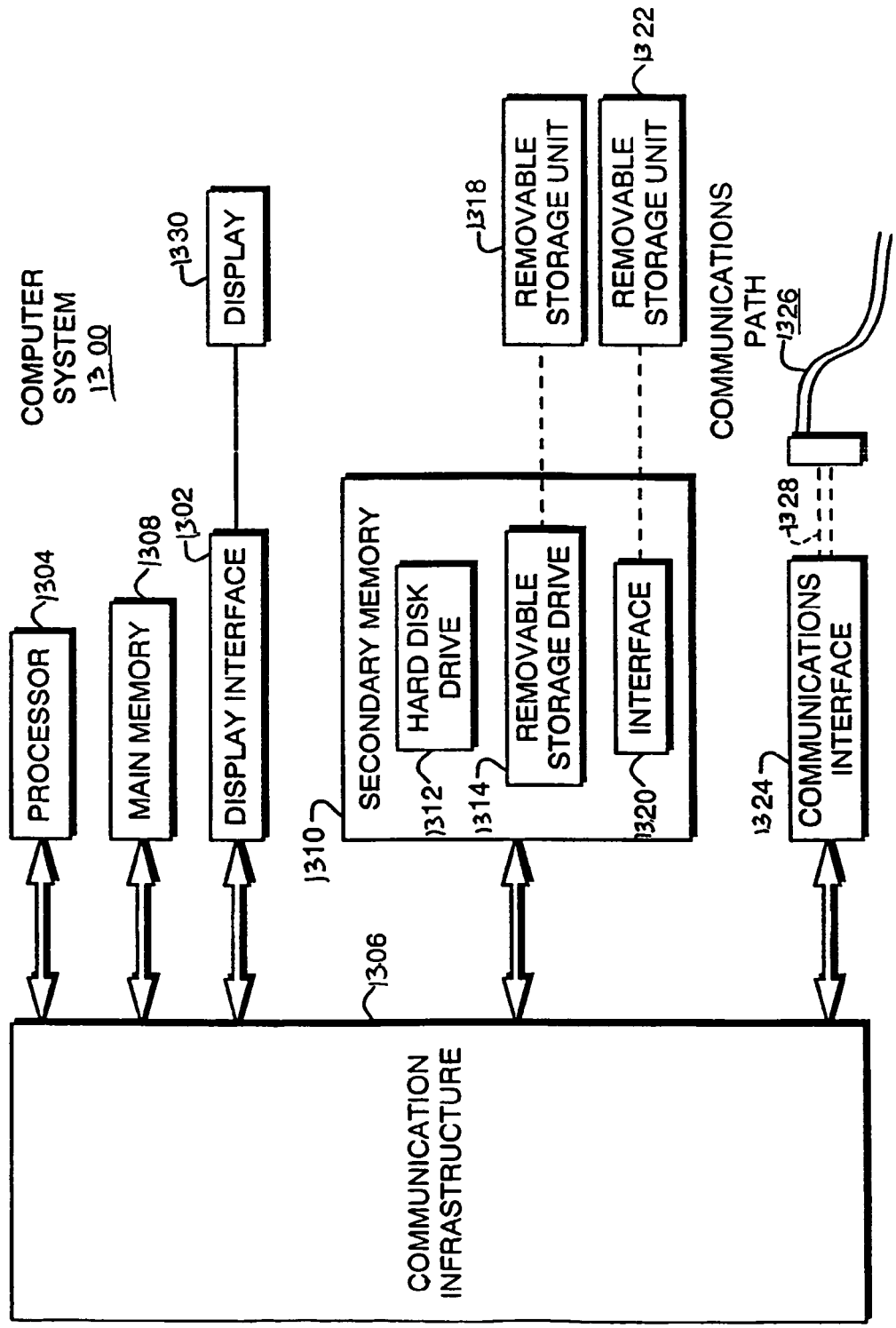
FIG. 13 is a functional block diagram for an illustrative computer system for implementation of the present invention.

The method and apparatus of the present invention (as discussed throughout this document) may be implemented using hardware, software or a combination thereof and may be implemented in one or more computer systems or other processing systems, or partially performed in processing systems such as personal digit assistants (PDAs). In an example embodiment, the invention was implemented in software running on a general-purpose computer 1300 as illustrated in FIG. 13. Computer system 1300 includes one or more processors, such as processor 1304. Processor 1304 is connected to a communication infrastructure 1306 (e.g., a communications bus, crossover bar, or network). Computer system 1300 includes a display interface 1302 that forwards graphics, text, and other data from the communication infrastructure 1306 (or from a frame buffer not shown) for display on the display unit 1330.

Computer system 1300 also includes a main memory 1308, preferably random access memory (RAM), and may also include a secondary memory 1310. The secondary memory 1310 may include, for example, a hard disk drive 1312 and/or a removable storage drive 1314, representing a floppy disk drive, a magnetic tape drive, an optical disk drive, etc. The removable storage drive 1314 reads from and/or writes to a removable storage unit 1318 in a well-known manner. Removable storage unit 1318, represents a floppy disk, magnetic tape, optical disk, etc. which is read by and written to by removable storage drive 1314. As will be appreciated, the removable storage unit 1318 includes a computer usable storage medium having stored therein computer software and/or data.

In alternative embodiments, secondary memory 1310 may include other means for allowing computer programs or other instructions to be loaded into computer system 1300. Such means may include, for example, a removable storage unit 1322 and an interface 1320. Examples of such removable storage units/interfaces include a program cartridge and cartridge interface (such as that found in video game devices), a removable memory chip (such as a ROM, PROM, EPROM or EEPROM) and associated socket, and other removable storage units 1322 and interfaces 1320 which allow software and data to be transferred from the removable storage unit 1322 to computer system 1300.

Computer system 1300 may also include a communications interface 1324. Communications interface 1324 allows software and data to be transferred between computer system 1300 and external devices. Examples of communications interface 1324 may include a modem, a network interface (such as an Ethernet card), a communications port, a PCM-CIA slot and card, etc. Software and data transferred via communications interface 1324 are in the form of signals 1328 which may be electronic, electromagnetic, optical or other signals capable of being received by communications interface 1324. Signals 1328 are provided to communications interface 1324 via a communications path (i.e., channel) 1326. Channel 1326 carries signals 1328 and may be implemented using wire or cable, fiber optics, a phone line, a cellular phone link, an RF link and other communications channels.

In this document, the terms "computer program medium" and "computer usable medium" are used to generally refer to media such as removable storage drive 1314, a hard disk installed in hard disk drive 1312, and signals 1328. These computer program products are means for providing software to computer system 1300. The invention includes such computer program products.

Computer programs (also called computer control logic) are stored in main memory 1308 and/or secondary memory 1310. Computer programs may also be received via communications interface 1324. Such computer programs, when executed, enable computer system 1300 to perform the features of the present invention as discussed herein. In particular, the computer programs, when executed, enable processor 1304 to perform the functions of the present invention. Accordingly, such computer programs represent controllers of computer system 1300.

In an embodiment where the invention is implemented using software, the software may be stored in a computer program product and loaded into computer system 1300 using removable storage drive 1314, hard drive 1312 or communications interface 1324. The control logic (software), when executed by the processor 1304, causes the processor 1304 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in Java, but could be implemented in other program languages, such as C++, that would be appreciated by those skilled in the art.

Studies Verifying the CI and the ABI:

Described below are the findings from three pilot studies that involved different subjects, different age groups, different genders, with data collection by different research assistants, in different facilities, using different EEG equipment. In summary, the results indicate that the CI: clearly differentiates ADHD from control subjects and correctly classifies over 80% of all subjects; discriminates, with almost no overlap, ADHD male subjects (age <16 years) from controls; correlates significantly with psychometric measures of ADHD; and is reliable over time and is positively influenced by methylphenidate.

Meta-analysis of the data: A total of 67 subjects, 33 ADHD and 34 control, participated in the pilot studies that we conducted and in a study conducted at Sweet Briar College. The sample consisted of 38 males and 29 females; 43 subjects were younger that 16 years. Analysis of variance with independent factors ADHD versus Control, Gender and Age group revealed that:

The average CI of ADHD subjects is 29% vs. 50% for controls, F=43.7, p<0.0001;
There was a significant Gender effect with males having a higher CI, F=4.1, p<0.05;
There was an age trend with younger subjects having higher CI, F=3.7, p=0.06;
There was a significant interaction between ADHD-control and Gender effects with males displaying stronger CI differences between ADHD and controls, F=5.6, p<0.05.

On the basis of the CI, a logistic regression model classified correctly 82% of all ADHD subjects and 77% of all control subjects with an overall classification accuracy of 80%. This model was statistically significant, p<0.0001. The classification power of the logistic model increased to 90% if only younger male subjects were included in the analysis. In addition, a Boolean decision-making rule based on the CI classified all but one of younger ADHD boys versus their age-gender-matched controls, a 96% correct classification.

From this analysis we can conclude that the CI is a highly significant discriminant of ADHD versus control subjects. In addition, with the specific subgroup of younger males it works extremely well on case-by-case basis classifying accurately almost 100% of these subjects in our pilot studies. This latter finding and the fact that younger males below age of 16 are the predominant ADHD population dictated our decision to describe this invention as a tool for screening and diagnosis boys, ages 8-16.

Detailed Results from Inventors' Pilot Studies

Figure 5:
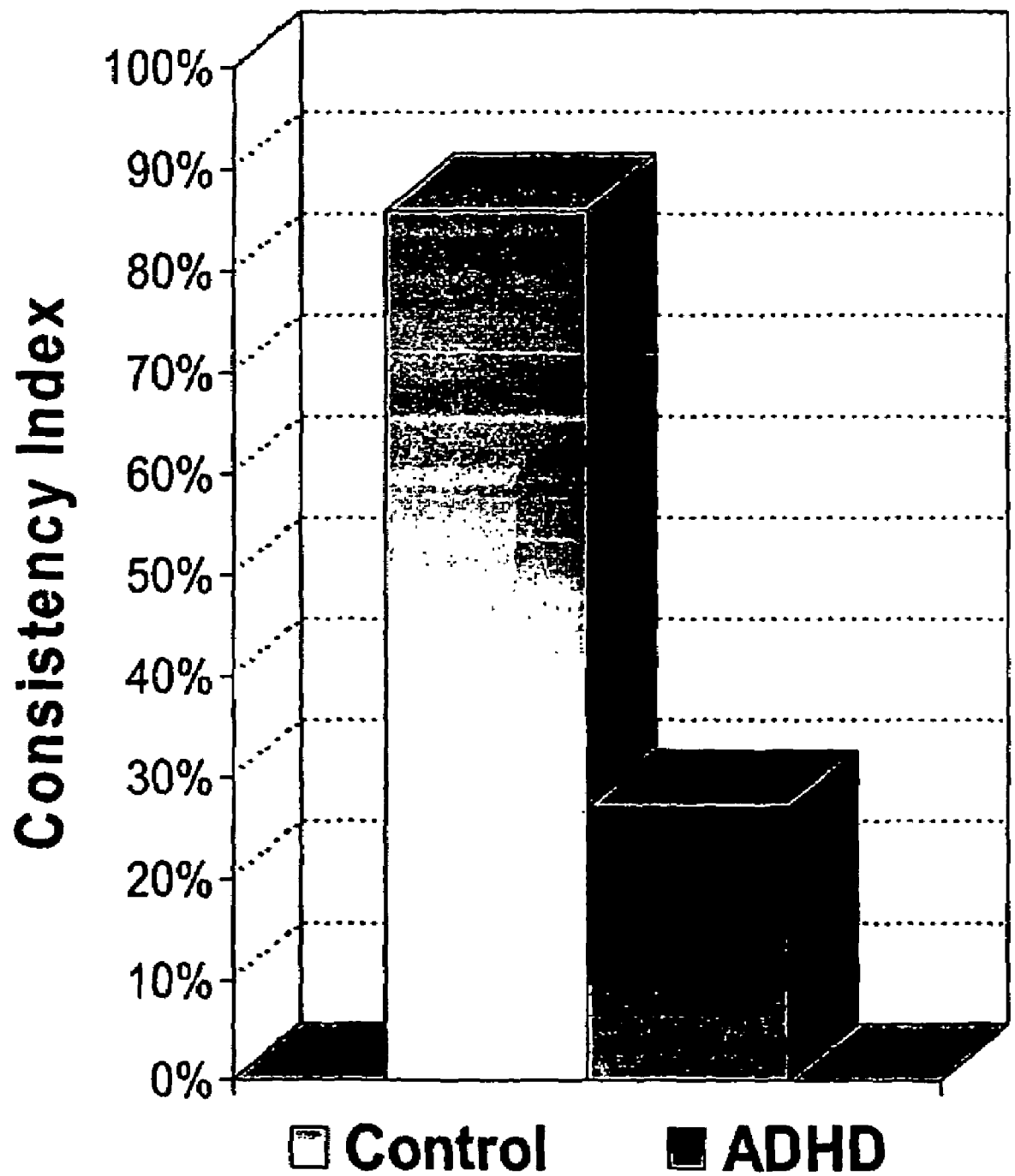
FIGS. 5 and 6 are results from pilot studies I and III, respectively, graphically presenting the CI for both a control group and the ADHD subjects.

Study I: Referring to table I below and FIG. 5, four boys, ages 6-10, with ADHD and four age-matched control boys tested at two 30-minute trials (video and reading) separated by a 5-minute break. For the ADHD boys, this procedure was repeated three months later, to assess test-retest reliability [34].

TABLE I

|  | ID | CI % | ADHD SI |
|---|---|---|---|
| Control | 101 | 100 | 2 |
|  | 102 | 75 | 0 |
|  | 107 | 75 | 0 |
|  | 108 | 94 | 2 |
| ADHD | 103 | 44 | 10 |
|  | 104 | 25 | 8 |
|  | 105 | 12 | 23 |
|  | 106 | 25 | 22 |

Group comparison: p = 0.0015
Correlation with ADHD SI: r = 0.84

Study II: Six ADHD males and six non-ADD) males, ages 18-25, participated in a double-blind, placebo versus methylphenidate controlled crossover design study. The subjects were given four tasks of the Gordon Diagnostic System, two easy (auditory and visual) and two hard (auditory and visual). Results have been submitted for publication in Cox, et al. [35]; and Merkel, et al. [36].

Figure 6:
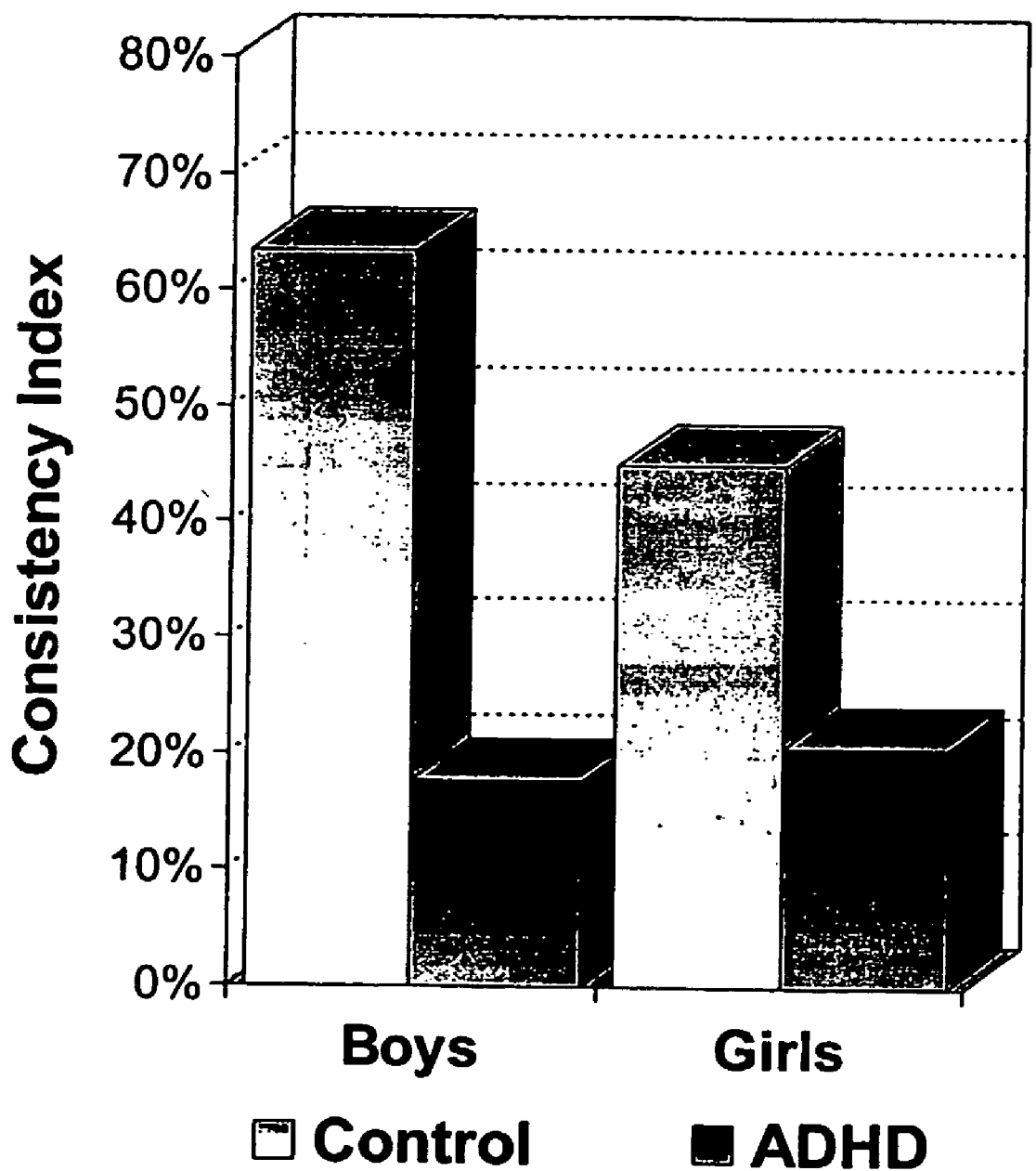

Study III: Referring to Table II below and FIG. 6, eighteen boys and seventeen girls, ages 8-16, classified as either ADHD or non-ADHD (9 boys and 8 girls with ADHD and 9 boys and 9 girls without ADHD) were tested for 36 minutes while performing various tasks (10 min. video, 1 min. break, 10 min. reading, 5 min. break, 10 min. math). The complete results have been submitted for publication in Kovatchev et al.[37].

TABLE II

|  | Boys | | Girls | |
|---|---|---|---|---|
|  | ID | CI % | ID | CI % |
| Control | 106 | 91 | 101 | 72 |
|  | 107 | 75 | 104 | 47 |
|  | 108 | 41 | 105 | 25 |
|  | 109 | 47 | 119 | 35 |
|  | 112 | 94 | 120 | 47 |
|  | 115 | 56 | 121 | 53 |
|  | 117 | 75 | 129 | 31 |
|  | 127* | 0 | 137 | 9 |
|  | 128 | 94 | 141 | 87 |
| ADHD | 102 | 25 | 114 | 0 |
|  | 111 | 19 | 126 | 40 |
|  | 116 | 3 | 131 | 31 |
|  | 123 | 22 | 134 | 59 |
|  | 124 | 3 | 135 | 0 |
|  | 125 | 28 | 138 | 34 |
|  | 130 | 44 | 139 | 0 |
|  | 132 | 16 | 140 | 0 |
|  | 136 | 0 | | |

*Identified by teacher as ADHD.
Group comparison, boys: p = 0.0008
Group comparison, girls: p = 0.03
Correlation with ADHD SI: r = 0.67

New Data and Recent Analyses

Figure 7:
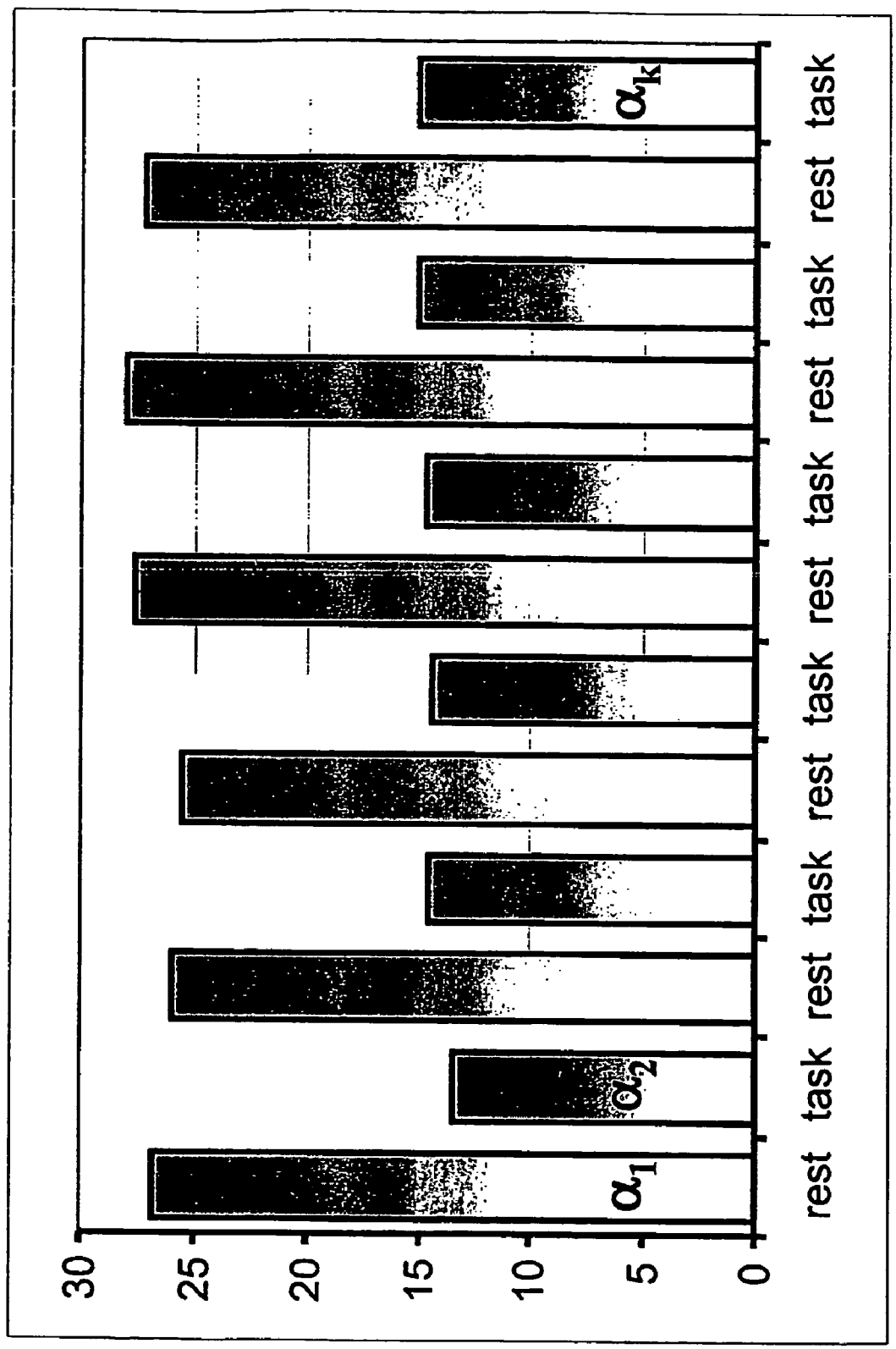
FIGS. 7 and 8 are results from pilot study IV, and graphically present the sequences of alpha-powers for a person without and with ADHD, respectively, that reflect high and low ABI.
Figure 8:
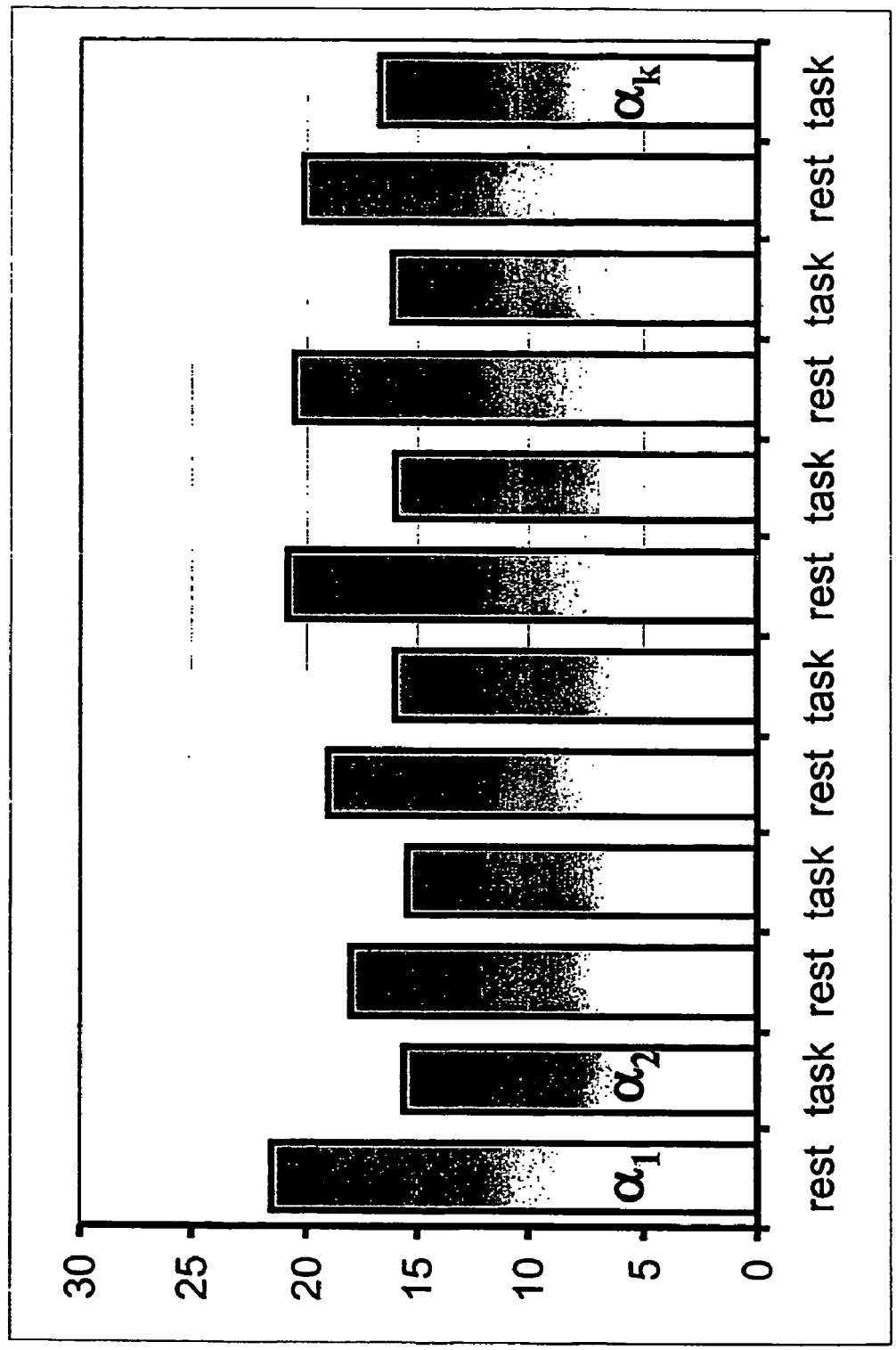

Study IV: EEG data for 30 female college students with ADHD and 30 female control college students with no ADHD tested on and off methylphenidate. Twelve data sets are included in the analysis below. In addition to higher CI, the analysis of the series of short tasks separated by short rest periods performed in the second half of the data collection revealed previously unknown, but very significant inconsistencies in the EEGs of female college students with ADHD relative to non-ADHD controls. ADHD subjects had (i) Less elevated alpha activity (vigilance) during rest periods, 20.0±1.3 vs. 26.8±1.0, p<0.001, and (ii) Less suppressed alpha activity during tasks, 15.9±0.4 vs. 14.5±0.6, p<0.001. These new findings resulted in the formulation of the Alpha Blockade Index. FIGS. 7 and 8 present the sequences of alpha-powers for a person without and with ADHD, respectively, that reflect high and low ABI.

Study V: In the study sponsored by the Commonwealth Health Research Board (CHRB), 77 children (67 males and 10 females, 36 ADHD and 41 non-ADHD) were administered EEGs. The comparison of ADHD versus control yielded a Consistency Index of 47% for the ADHD subjects and a Consistency Index of 65% for the control subjects, F=9.0, p<0.005. This confirmed our primary hypothesis that lower Consistency Index is associated with ADHD.

The optimal classification threshold of the Consistency Index was found to be 40%, which confirmed the results from our pilot studies (e.g. a Consistency Index of 40% or less is considered to be a sign of ADHD). Twenty out of 30 ADHD boys had $CI_1$ of 40% or less, which implies that the Consistency Index confirmed 66% of the initial diagnosis of ADHD. Thirty out of 33 controls had $CI_2$ above 40%, which implies that the Consistency Index had over 90% specificity. These results meet our expectations that the Consistency Index would confirm most non-ADHD boys and would reject some of the initial diagnoses of ADHD (one-third of the cases in this study). The latter confirms our hypothesis that the determination of ADHD based solely on background questionnaires and interviews may be resulting in over-diagnosis of the disorder.

Study VI: Having an objective, reliable diagnostic procedure could also be used to assess the effectiveness of treatment in persons with ADHD. This could be achieved by demonstrating whether the treatment being considered appropriately impacts on the EEG parameters of concern.

In the most recent study funded by McNeil Consumer Health Care, the inventors evaluated six males with ADHD or ADD, both on and off methylphenidate. This study was conducted to examine the effects of medication on driving ability, but the inventors also collected EEG data for subjects while on and off medication. Subjects were between the ages of 16-19, and reported a previous positive response to methylphenidate. Four of 6 ADHD subjects obtained a Consistency Index (CI) of 40% or lower when taking no medication. One subject was sleepy during the no medication EEG and obtained a CI of 100, which is predicted with this state. Therefore, his CI from the no medication trial is most likely invalid. Significantly, all subjects displayed an increase in their CI when tested on Ritalin, and all but one subject achieved a CI of 50% or more when on Ritalin. A CI of 50% or more is associated with normal or consistent cognitive transition, and is considered to be indicative of the absence of ADHD or ADD.

This study confirmed the hypotheses that lower EEG consistency during transitions from one cognitive task to another (Consistency Index of <40%) will be a significant physiological marker associated with individuals with ADHD or ADD. That the EEG CI will increase or normalize ($CI \geq 50\%$) in individuals with ADHD or ADD who are treated with appropriate doses of methylphenidate.

Stochastic Model

A third aspect of the present invention shall provide a method, apparatus, and computer program product for providing a sequential or non-sequential stochastic model procedure that would be utilized to diagnose attentional disorders, provide neurofeedback treatment, and evaluate treatment response. The present invention sequential stochastic procedure is an optimization of several components used to diagnose or mark attentional or cognitive deficits or impairments. These components include several sequential assessments, some of which would be disease specific, and some of which would be general to all attentional/cognitive impairment: a) psychometric data (in vivo and by history); b) behavioral data; c) EEG acquisition involving assessment of CI1 and CI2 (to access large temporal scale): and d) EEG acquisition involving rapid succession of 1-minute cognitive tasks (to access intermediate temporal scale). Each of the sequential steps contributes to the assessment of the condition and the final diagnosis is based upon the combination of all or substantially all.

Summarily and as set forth immediately below, the algorithms comprise, but not limited thereto the following procedures integrated by a sequential stochastic classification model:

a) Psychometric assessment—standardized test protocol for screening and evaluation of persons for presence/absence of symptoms of cognitive attentional impairment:
  i) Standard ADHD psychometrics.
  ii) Psychometrics evaluating the ability for attentional shifts, specifically the Assessment of Cognitive Transition Difficulty (ACTD), and related neuropsychological assessments.

b) Electroencephalographic (EEG) data acquisition procedure comprised of two sessions:
  i) Cognitive Transition Protocol ("Transition Protocol"), consisting of about two 10-minute cognitive tasks separated by about a 5-minute structured rest.
  ii) Rapid Cognitive Transition Protocol ("Rapid Transition Protocol"), consisting of a rapid sequence of changing about 2-minute tasks separated by about 1-minute rests.

c) Mathematical model of EEG transition consistency for ADHD based on EEG acquisition:
  i) Transition Protocol Consistency Index (CI) for quantifying the lack of attentional transition between the tasks, corresponding to the slow part above. The CI has two versions distinguished by different summation formulas as described previously.
  ii) Rapid Transition Protocol Alpha Blockade Index (ABI) for quantifying less elevated alpha activity (vigilance) during rest periods, corresponding to the fast part of the data collection.

d) EEG Data analysis algorithms and software that follow this model.

e) Stochastic assessment procedure merging the psychometrics, the EEG data, and the results form the mathematical models into a single diagnostic instrument.

The present invention method pertains directly to enhancement of existing psychological, behavioral, and physiological EEG data acquisition systems by introducing a sequential stochastic model procedure, and an intelligent data interpretation component capable of assessing EEG inconsistencies associated attentional impairments. Potential users of this product will be any person or organization that diagnoses or treats persons with attentional or cognitive impairments. Upon approval, the method can be used for initial screening and diagnosis of disorders associated with impaired attention, such as ADHD, as well as for treatment and evaluation of the effects of treatments, such as medication or additional therapies.

Regarding the demographic assessment, the method includes standard demographic questions such as age, gender, etc., and surveys about family and school environment.

Psychometric data includes standard ADHD scales and specifically developed questionnaires that measure attentional transitions. For example, for standard psychometrics, psychological data regarding general attention (i.e., MMSE) is obtained, and then data regarding disease or disorder specific cognitive/attentional impairments is obtained via assessment questionnaires, scales, and inventories specific to the disorder, (i.e., the DuPaul Rating Scale for ADHD). In addition, neuropsychological findings (such as the results of the PASAT), as well as behavioral ratings (in vivo) are incorporated. Whereas for psychometrics that evaluates the ability for attentional shifts, data regarding the difficulty of cognitive transition is obtained via the Assessment of Cognitive Transition Difficulty (ACTD).

Turning to the present invention stochastic assessment procedure, this model employs several sequential dependent assessments to increase the probability of a reliable and valid diagnosis of attentional impairment. Each dependent measure is geared towards gathering pertinent data specific to the particular domain (psychological, behavioral, physiological), so that all domains are assessed and predictive validity is maximized. In the next step, the physiological aspects of the EEG data are obtained, calculated and incorporated into the model. These EEG measures include the CI and ABL as measured by alpha blockade during multiple alternating minute long cognitive tasks. Thus, the final diagnosis/assessment is based upon the mathematical combination of all of the above psycho-physiological data, and therefore, has increased specificity/sensitivity beyond any single measure.

Figure 9:
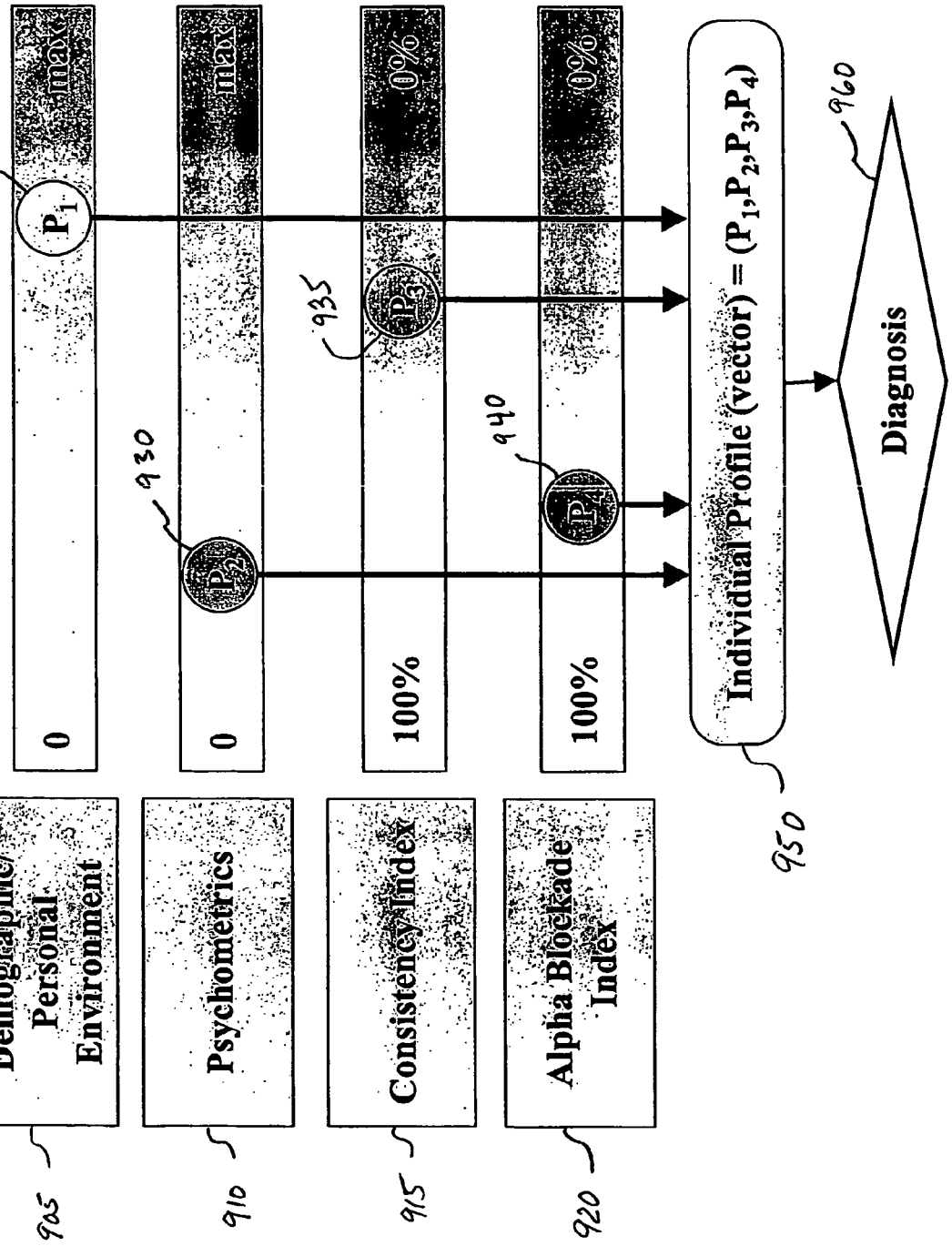
FIG. 9 is a schematic illustration of the multidimensional individual profile of the present invention stochastic classification method.

Formal data representation. Turning to FIG. 9, the data for each subject, the subject's individual profile 950, is represented as a vector comprising personal and demographic/environmental information 905, psychometric scores 910, CI 915, and ABI 920. Thus, each subject is represented as a point in a multi-dimensional space, corresponding to the coordinates of the individual profile vector 950.

Diagnostic Assessment Algorithm

The basic unit of the algorithm is a single step assigning a personal probability for attentional impairment based on the assessment of the personal profile at each specific step as follows. It should be appreciated that the probability ranges as set forth below in steps 1-4 are intended to be illustrated rather than limiting and other desired ranges may be implemented practiced as well. The steps can be practiced in alternate orders than as listed below.

Step 1—Demographic assessment.
For the demographic data this will be done based on population prevalence data in different sub-populations defined by age, gender, etc. At this step every subject is assigned a probability of attentional impairment, $P_1$ 925. For example, a 19 year old female will receive prior probability of attentional impairment p=0.005 while an 8 year old boy will be assigned probability 0.12. In general the demographic assessment will be used to establish prior probabilities of attentional impairment for each subject.

Step 2—Psychometric assessment.
Pertaining to psychometrics, a probability for attentional impairment $P_2$ 930 will be assigned based on the standard scales and the Assessment of Cognitive Transition Difficulty (ACTD) in the following manner: p=1.0, for a definitive attentional impairment classification, p=0.0 for a definitive non-impairment classification. P=0.5 for unclear cases.

Step 3—Consistency Index.
Pertaining to the CI, the probability for attentional impairment $P_3$ 935 at this step is p=0 if CI>60%; p=1 if CI<40%, and p=0.5 otherwise.

Step 4—Alpha Blockade Index.
The probability attentional impairment $P_4$ 940 at this step is p=0 if AI>40%; p=1 if CI<20%, and p=0.5 otherwise.

Figure 10:
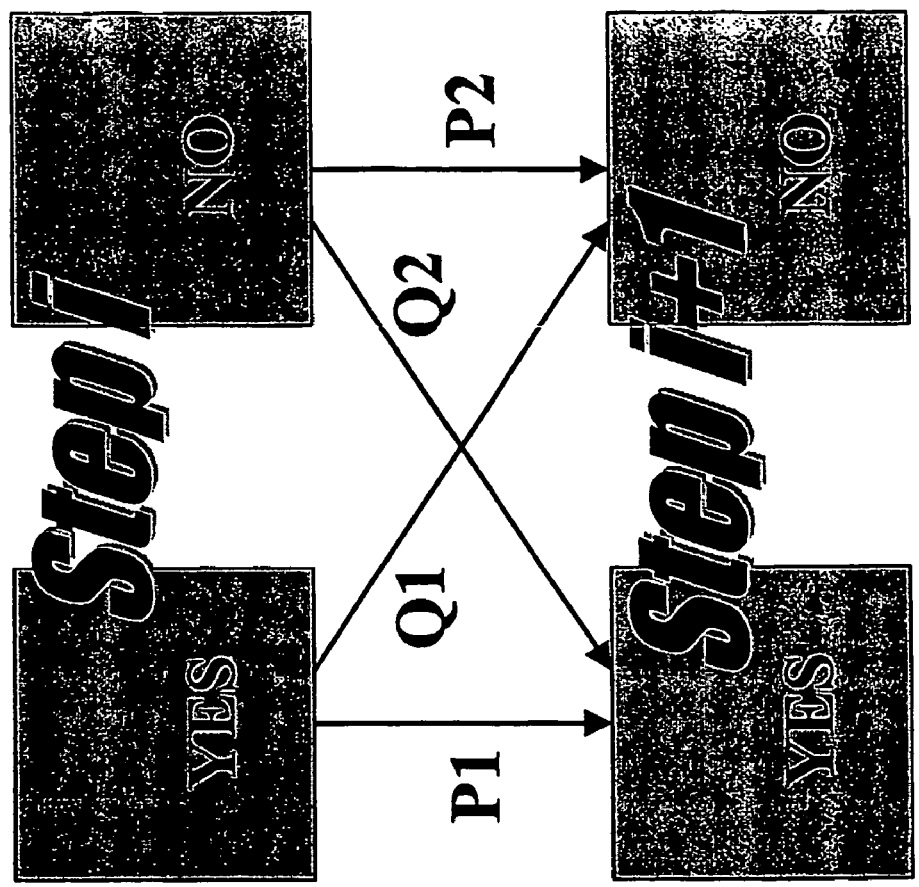
FIG. 10 is a schematic illustration of the stochastic transition linking at least some of the steps illustrated in FIG. 9.

In addition, referring to FIG. 10, the above steps are linked by computing the conditional probabilities of attentional impairment / non-impairment at each step, given the assessment at a previous or posterior step(s). It is contemplated that some steps may be omitted from the linking.

Figure 11:
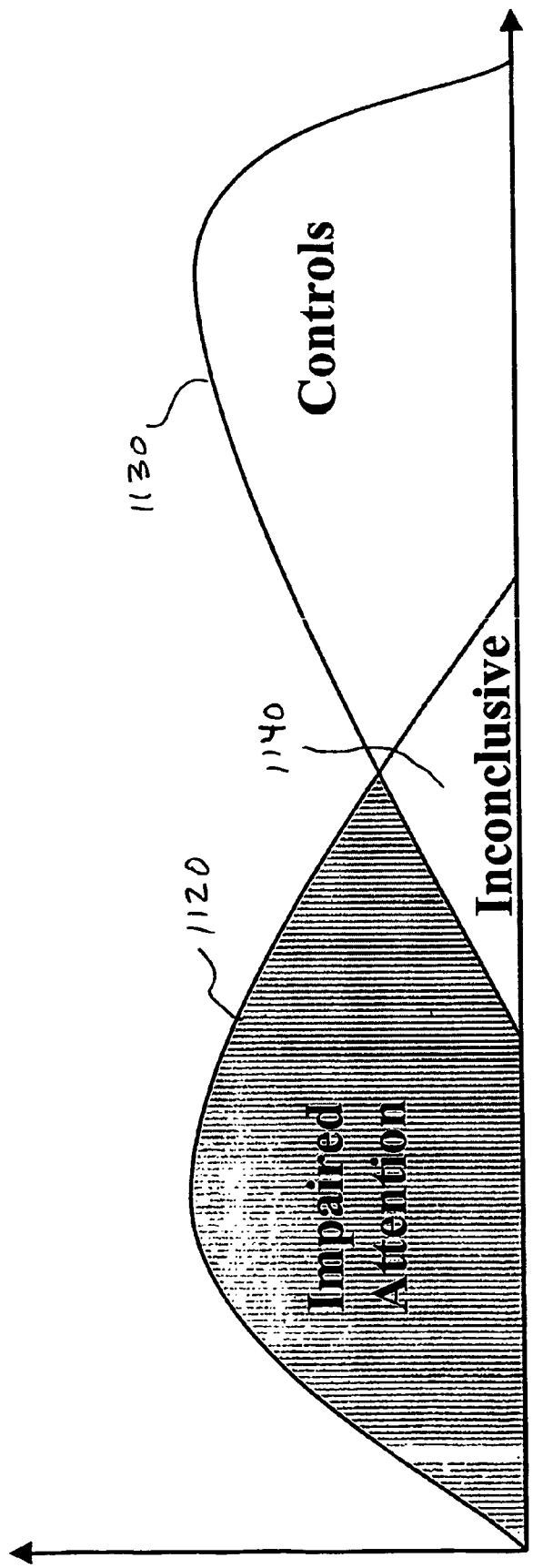
FIG. 11 graphically illustrates the probablity density function for an impaired attention group and the control group as determined from a stochastic model analysis.

Turning to FIG. 11, FIG. 11 graphically illustrates the probability density function for an impaired attention group 1120 and the control group 1130 as determined from a stochastic model analysis. Since at each step we have a "gray zone" of a non-definitive assessment 1140, the final result of the sequential computations will be a probability that the assessed person has attentional impairment. FIG. 11 illustrates the distributions of these probabilities for attentional impairment/non-impairment populations. The distributions are expected to overlap, thus identifying a subgroup of individuals with no definitive diagnosis. However, at each iterative or repetitive step of the assessment, the overlap zone becomes smaller and the final result is an assessment that is substantially more precise than any of its individual steps.

Treatment Assessment Algorithm

A major disadvantage of the psychometric criteria is that they do not provide means for immediate assessment of the effectiveness of a treatment. In contrast, the results from both the present invention Cognitive Transition and Rapid Cognitive Transition EEG protocols are available within minutes (the Fast EEG protocol provides even almost on-line tracking of attentional shifts) and therefore the CI and the ABI can be used as indicators of the effectiveness of a treatment procedure.

Figure 12:
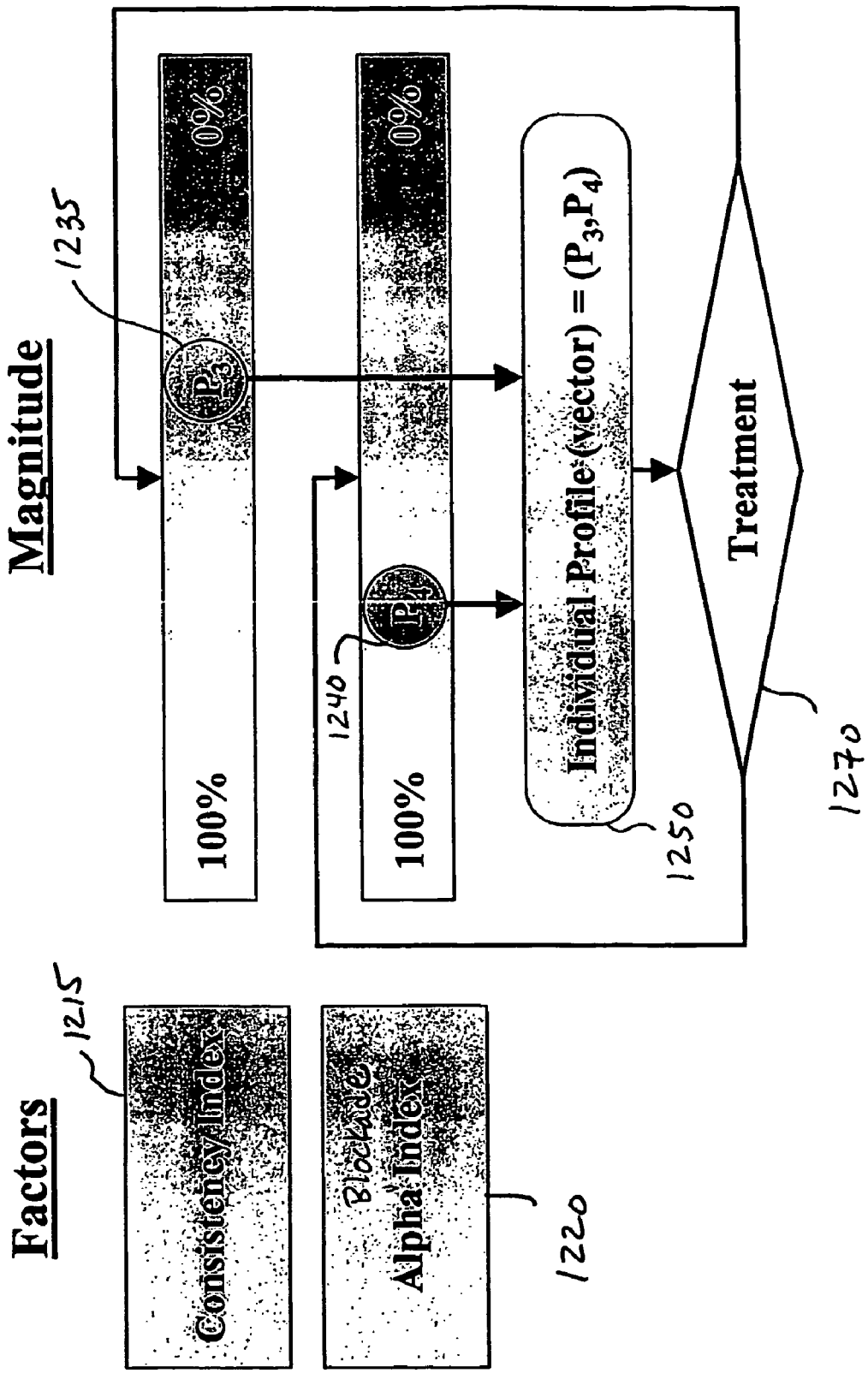
FIG. 12 graphically illustrates the assessment of treatment effectiveness for treatment procedures.

As illustrated in FIG. 12, the Treatment Assessment Algorithm includes the last two steps of the Diagnostic Assessment Algorithm embedded into recursive loop containing the treatment. The algorithm evaluates shifts in the probability of attentional impairment that may result from the treatment. A successful treatment would increase the personal probability for non-impairment, shifting the attentional impairment probability distribution of FIG. 11 toward the non-impairment zone. Measuring such shifts allows the present invention method, apparatus, and computer program product to: 1) immediately assess treatment effectiveness, 2) compare treatments (since the output is standardized), 3) evaluate duration of treatment effects (provided that the assessment is performed several times throughout the course of treatment), and 4) the Rapid Transition EEG protocol and the ABI provide on-line feedback and thus opportunity for biofeedback-based treatment procedures.

In conclusion, an advantage of the present invention is that it provides, among other things, a standardized test protocol for screening and evaluation of attentional impairment. That includes a combination of psychological and physiological assessments. The present invention method and apparatus is built upon the notion that most significant markers of attentional impairment arise when subjects shift their attention from one task to another, and that this phenomenon can be quantified by a combination of psychometrics and measures derived from EEG data. Preliminary studies suggest that the method is most precise for screening and diagnosis of ADHD among boys, 8 to 16 years of age, but is also effective for other gender age groups, including adolescent males and college females.

Another advantage of the present invention is that it provides method, apparatus, and computer program product that pertains directly to the enhancement of existing psychological, behavioral, and physiological EEG data acquisition systems by introducing a sequential stochastic model procedure, and an intelligent data interpretation component capable of assessing EEG inconsistencies associated attentional impairments. Potential users of this product will be any person or organization that diagnoses or treats persons with attentional or cognitive impairments. Upon approval, the present invention method can be used for initial screening and diagnosis of disorders associated with impaired attention, such as ADHD, as well as for treatment and evaluation of the effects of treatments, such as medication or additional therapies.

Further yet, the present invention will provide a relatively simple diagnostic procedure that will lead to better screening and treatment of attentional impairment, and the prevention of overmedication. It will further provide an inexpensive and clear method for diagnosis of ADHS and other impairments.

Finally, the present invention provides a comprehensive, flexible, and an effective diagnostic measure of attentional abilities, as well as an indicator for treatment effectiveness and rehabilitation progress.

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced herein.

REFERENCES

The following articles, publications, patent applications, and patents are hereby incorporated by reference in their entirety herein:

1. Ritchie, K., Artero, S., & Touchon, J., 2001. Classification criteria for mild cognitive impairment: A population based validation study. *Neurology*, 56(1), 37-42.
2. Ballard, C, O'Brien, J. Gray, A., Cormack, F., Ayre, G., Rowan, E. H., Thompson, P., Bucks, R., McKeith, I., Walker, M., & Tovee, M., 2001. Attention and Fluctuating Attention in Patients with Dementia with Lewy Bodies and Alzheimer Disease. *Archives of Neurology*, 58(6), 977-982.
3. Grodstein, F., Chen, J., Wilson, R., & Manson, J., 2001. Type 2 Diabetes and Cognitive Function in Community Dwelling Elderly Women. *Diabetes Care.* 24(6), 1060-1065.
4. Sohlberg, M. & Mateer, C., 2001. Improving Attention and Managing Attentional Problems: Adapting Rehabilitation Techniques to Adults with ADD. *Annals of New York Academy of Sciences,* 931, 359-375.
5. Armstrong, C., Hayes, K, & Martin R., 2001. Neurocognitive Problems in Attention Deficit Disorder: Alternative Concepts and Evidence for Impairment in Inhibition of Selective Attention. *Annals of New York Academy of Sciences,* 931, 196-215.
6. Levin, H., Rossman, R., Rose, J., et al., 1979. Long-term neuropsychological outcome of closed head injury. *Journal of Neurosurgery,* 50, 412-422.
7. Meyer, J., Rauch, G., Rauch, R., Haque, A., & Crawford, K., 2000. Cardiovascular and Other Risk Factors for Alzheimer's Disease and Vascular Dementia. *Annals of New York Academy of Sciences,* 903, 411-423.
8. Chang, L, Speck, O., Miller, E., Braun, J., et al., 2001. Neural correlates of attention and working memory deficits in HIV patients. *Neurology,* 57(6), 1001-1007.
9. ADHD, NIH Consensus Statement, 1998. Diagnosis and Treatment of Attention Deficit Hyperactivity Disorder. November 16-18.
10. Pohjasvaara, T., Ylikoski, R., Leskela, M., et al., 2001. Evaluation of Various Methods of Assessing Symptoms of Cognitive Impairment and Dementia. *Alzheimer Disease and Associated Disorders,* 15(4), 184-193.
11. Lezak, M., Neuropsychological Assessment, Second Edition. New York: Oxford University Press, 1995.
12. Rosen, W., Mohs, R., & Davis, K., 1984. A new rating scale for Alzheimer's disease. *American Journal of Psychiatry,* 141, 1356-1364.
13. Doraiswamy, P., Kaiser, L., Bieber, F., & Garman, R., 2001. The Alzheimer's Disease Assessment Scale: Evaluation of Psychometric Properties and Patterns of Cognitive Decline in Multicenter Clinical Trials of Mild to Moderate Alzheimer's Disease. *Alzheimer Disease and Associated Disorders.* 15(4), 174-183.
14. MacArthur, J., Hoover, D., Bacellar, H., et al., 1993. Dementia in AIDS patients: incidence and risk factors. *Neurology,* 42, 2245-2252.
15. MacArthur, J., Cohen, B., Slenes, O., et al., 1989. Low prevalence of neurological and neuropsychological abnormalities in other wise healthy HIV-1 infected individuals: Results from the Multicenter AIDS Cohort Study. *Annals of Neurology,* 26, 601-611.
16. Heaton, R., Grant, I., Butters, N., et al., 1995. The HNRC Neuropsychology of HIV infection at different stages. HIV Neurobehavioral Research Center. *Journal of International Neuropsychology Society,* 58, 231-251.
17. American Psychiatric Association, 1994. *Diagnostic and statistical manual of mental disorders* (4th ed.). Washington, D.C.: American Psychiatric Association.
18. Goldman, L. S., Genel, M., Bezman, R. J., and Slanetz, P. J. (1998). Council report of diagnosis and treatment of Attention-Deficit Hyperactivity Disorder in children and adolescents. *Journal of the American Medical Association,* 279, 1100-1107.
19. Wolraich, M. L. & Baumgaertel, A., 1996. The prevalence of Attention Deficit Hyperactivity Disorder based on the new DSM-IV criteria. *Peabody Journal of Education,* 71, 168-186).
20. Hebert, L., Beckett, L., Scherr, P., & Evans, D., 2001. Annual Incidence of Alzheimer Disease in the United States Projected to the Years 2000 through 2050. *Alzheimer Disease and Associated Disorders,* 15(4), 169-173).
21. Barkley, R. A., Guevremont, D. C., Anastopoulos A. D., DuPaul G. J., & Shelton T. L., 1993. Driving-related risks and outcomes of attention deficit hyperactivity disorder in adolescents and young adults: a 3- to 5-year follow-up survey. *Pediatrics,* 92, 212-218.
22. Zametkin, A. J. & Rapoport, J. L., 1987. Neurobiology of attention deficit disorder with hyperactivity: where have we come in 50 years? *Journal of the American Academy of Child and Adolescent Psychiatry,* 26, 676-686.
23. Crawford, H. & Barabasz, M., 1996. Automated EEG magnitudes in children with and without attention deficit disorder during neurological screening and cognitive tasks. *Child Study Journal,* 26, 71-86.
24. Dykman, R. A., Holcomb, P. J., Oglesby, D. M., & Ackerman, P. T., 1982. Electrocortical Frequencies in Hyperactive, Learning-Disabled, Mixed, and Normal Children. *Biological Psychiatry,* 17(6), 675-685).
25. Satterfield, J., Schell, A., Backs, R., & Hidaka, K., 1984. A Cross-sectional and longitudinal study of age effects of electrophysiological measures in hyperactive and normal children. *Biological Psychiatry,* 19(7), 973-990).
26. Mann, C. A., Lubar, J. F., Zinmmerman, A. W., Miller, C. A., Muenchen, R. A., 1992. Quantitative analysis of EEG in boys with attention-deficit-hyperactivity disorder: Controlled study with clinical implications. *Pediatric Neurology,* 8, 30-36.
27. Janzen, T., Graap, K., Stephanson, S., Marshall, W., Fitzsimmons, G., 1995. Differences in baseline EEG measures for ADD and normally achieving preadolescent males. *Biofeedback and Self Regulation,* 20, 65-82.28. Clarke, A. R., Barry, R. J., McCarthy, R., Selikowitz, M., 1998. EEG analysis in attention-deficit/hyperactivity disorder: A comparative study of two subtypes. *Psychiatry Research,* 81, 19-29.

29. Ackerman, P. T., Dykman, R. A., Oglesby, D. M., Newton, J. E. O., 1994. EEG power spectra of children with dyslexia, slow learners, and normally reading children with ADD during verbal processing. *Journal of Learning Disabilities,* 27 (10), 619-630.

30. Chabot, R. & Serfontein, G., 1996. Quantitative Electroencephalographic profiles of children with attention deficit disorder. *Biological Psychiatry,* 40 (10), 951-963.

31. Douglas, V., 1998. Cognitive control processes in ADHD. In Quay, H., Hogan, A., (Eds.) *Handbook of Disruptive Behavior Disorders.*

32. McDonald, S., Bennett, K., Chambers, H., and Castiello, U., 1999. Covert orienting and focusing of attention in children with attention deficit hyperactivity disorder. *Neuropsychologia,* 37 (3), 345-356.

33. Andreassi, J. L., 1989. *Psychophysiology: Human behavior and physiological response.* Hillsdale, N.J.: Erlbaum.

34. Cox, D. J., Kovatchev, B. P., Morris, J. B., Philips, C., Hill, R., and Merkel, L. (1999). Electroencephalographic and Psychometric Differences Between Boys With and Without Attention Deficit/Hyperactivity Disorder (ADHD)—A Pilot Study. *Applied Psychophysiology and Biofeedback,* 23: 179-188.

35. Cox, D. J., Merkel, R. L., Kovatchev, B. P., and Seward, R. Attention Deficit/Hyperactivity Disorder (ADHD) Impairs Driving Performance, which is Remedied with Stimulant Medication: A Preliminary Double Blind Placebo Controlled Trial. *Applied Psychophysiology and Biofeedback.* In press.

36. Merkel, R. L., Cox, D. J., Kovatchev, B. P., Morris, J., Seward, R., Hill, R., and Reeve, R. (2000). The EEG Consistency Index as a measure of Attention Deficit/Hyperactivity Disorder and responsiveness to medication: A Double blind placebo controlled pilot study. *Journal of Applied Psychophysiology.* In press.

37. Kovatchev, B. P., Hill, R., Morris, J. B., Reeve, R., Robeva, R. S., Loboschefski, T., and Cox, D. J. EEG Transition Consistency and its Relationship to ADHD: Validation of the Consistency Index. In press.

38. Goldstein, S., & Ingersoll, B., 1993. Controversial treatments for children with ADHD and impulse disorders. In *Handbook of childhood impulse disorders and ADHD: Theory and practice.* C. C. Thomas Publisher, Springfield: Ill.

We claim:

1. A method for assessing individuals for disorders associated with attentional impairments, said method comprising:
    a) placing at least one electrode at a respective cranial site on an individual;
    b) obtaining digitized EEG data at epochs of a plurality of frequency bands, said EEG data collected from a first cognitive task period, a rest period, and a second cognitive task period, wherein: the individual performs predetermined tasks during said first and second cognitive task periods, and the individual rests during said rest period;
    c) processing said EEG data to determine electrophysical power (pW) obtained from said first cognitive task period and said second cognitive task period;
    d) calculating the power change distance (PCD) between said first and second cognitive task periods;
    e) filtering said PCD data by comparing said PCD data with a noise threshold number;
    f) applying a cutoff frequency dividing said filtered PCD data into two ranges, a first range being PCD data below said cut-off frequency and a second range being PCD data above said cut-off frequency;
    g) calculating a Consistency Index, said Consistency Index being defined by the absolute value of the difference between a sum of said below cut-off PCD data and a sum of said above cut off PCD data; and
    h) comparing said Consistency Index to a control group database to provide the assessment of the individual.

2. The method of claim 1, wherein calculating said PCD in step (d) is calculated using the following formula:

$$PCD = \frac{M1 - M2}{\sqrt{\frac{SD1^2}{N1} + \frac{SD2^2}{N2}}}$$

wherein M1 and M2 are the mean powers at two contiguous tasks, SD1 and SD2 are their standard deviation, and N1 and N2 are the epoch counts at said cognitive task periods.

3. The method of claim 2 wherein filtering said PCD data in step (e) comprises: comparing said PCD data with said noise threshold number, wherein any said PCD that are larger by an absolute value than said threshold value are marked by 1 or −1 depending on their direction, and whereas any said PCD below threshold are marked by zero, whereby filtering transforms said PCD into a sequence of 1, 0, −1.

4. The method of claim 3, wherein said noise threshold number is a number or range of numbers ranging from about 1.5 to about 4.0.

5. The method of claim 3, wherein calculating said Consistency Index of step (g) is calculated using the following formula:

$$CI = 100 \left| \frac{1}{N} \left( \sum_{belowcutoff\ f} \delta_i - \sum_{abovecutoff\ f} \delta_j \right) \right| \text{percent,}$$

% wherein $\delta_i, \delta_j = -1, 0, 1$.

6. The method of claim 1, wherein:
    said first cognitive task period has a duration within a range of about 8 to about 25 minutes; said rest period has a duration within a range of about 3 to about 8 minutes; and said second cognitive task period has a duration within a range of about 8 to about 25 minutes.

7. The method of claim 6, wherein: said first cognitive task period has a duration within a range of about 9 to about 11 minutes; said rest period has a duration within a range of about 4 to about 6 minutes; and said second cognitive task period has a duration within a range of about 9 to about 11 minutes.

8. The method of claim 7, wherein: said first cognitive task period has a duration of about 10 minutes; said rest period has a duration of about 5 minutes; and said second cognitive task period has a duration of 10 minutes.

9. The method of claim 1, wherein the individual during said first and second cognitive task periods participate in an activity selected from the group consisting of:
    reading, performing math, viewing video, tracking on a computer screen, and listening.

10. The method of claim 1, wherein said digitized EEG data in step (b) is obtained by utilizing a Fast Fourier Transform analysis.

11. The method of claim 1, wherein said digitized EEG data in step (b) is obtained in four frequency bands: Theta (4-8 Hz), Alpha (8-14 Hz), Beta (13-22 Hz) and High Beta (22-40 Hz).

12. The method of claim 1, wherein number of electrodes range from 1 to 15.

13. The method of claim 1, wherein the disorders include at least one of mild cognitive impairment (MCI) in individuals with pre-dementia, dementia, dementia with Lewy bodies, Alzheimer's Disease, traumatic brain injury, Attention Deficit/Hyperactivity Disorder (ADHD), and cognitive/attentional declines associated with chronic diseases such as diabetes, cardiovascular disease, and HIV infection.

14. The method of claim 1, wherein the assessment of the individual is utilized to determine the type of medication or other treatment or the amount of medication or other treatment or both the type and the amount to be prescribed to the individual for treating the disorder.

15. The method of claim 1, wherein as the individuals receive a course of treatment for any of the disorders, the method further comprises: repeating steps (a) through (g) at least one or more times over a select duration to determine success or efficacy of the treatment.

16. An apparatus for assessing individuals for disorders associated with attentional impairments, said apparatus comprising:
an EEG device having at least one electrode adapted for attachment at a respective cranial site on an individual, said EEG device obtaining digitized EEG data at epochs of a plurality of frequency bands, said EEG data collected from a first cognitive task period, a rest period, and a second cognitive task period, wherein: the individual performs predetermined tasks during said first and second cognitive task periods, and the individual rests during said rest period;
a processor programmed to:
a) process said EEG data to determine electrophysical power (pW) obtained from said first cognitive task period and said second cognitive task period;
b) calculate the power change distance (PCD) between said first and second cognitive task periods;
c) filter said PCD data by comparing said PCD data with a noise threshold number;
d) apply a cutoff frequency dividing said filtered PCD data into two ranges, a first range being PCD data below said cut-off frequency and a second range being PCD data above said cut-off frequency;
e) calculate a Consistency Index, said Consistency Index being defined by the absolute value of the difference between a sum of said below cut-off PCD data and a sum of said above cut off PCD data; and
f) compare said Consistency Index to a control group database to provide the assessment of the individual.

17. The apparatus of claim 16, wherein calculating said PCD in step (d) is calculated using the following formula:

$$PCD = \frac{M1 - M2}{\sqrt{\frac{SD1^2}{N1} + \frac{SD2^2}{N2}}}$$

wherein M1 and M2 are the mean powers at two contiguous tasks,
SD1 and SD2 are their standard deviation, and
N1 and N2 are the epoch counts at said cognitive task periods.

18. The apparatus of claim 17 wherein filtering said PCD data in step (e) comprises: comparing said PCD data with said noise threshold number, wherein any said PCD that are larger by an absolute value than said threshold value are marked by 1 or −1 depending on their direction, and wherein any said PCD data below threshold are marked by zero, whereby filtering transforms said PCD into a sequence of 1, 0, −1.

19. The apparatus of claim 18, wherein said noise threshold number is a number or range of numbers ranging from about 1.5 to about 4.0.

20. The apparatus of claim 18, wherein calculating said Consistency Index of step (g) is calculated using the following formula:

$$CI = 100 \left| \frac{1}{N} \left( \sum_{belowcutof\ f} \delta_i - \sum_{abovecutof\ f} \delta_j \right) \right| percent,$$

% wherein $\delta_i, \delta_j = -1, 0, 1$.

21. The apparatus of claim 16, wherein: said first cognitive task period has a duration within a range of about 8 to about 25 minutes; said rest period has a duration within a range of about 3 to about 8 minutes; and said second cognitive task period has a duration within a range of about 8 to about 25 minutes.

22. The apparatus of claim 21, wherein: said first cognitive task period has a duration within a range of about 9 to about 11 minutes; said rest period has a duration within a range of about 4 to about 6 minutes; and said second cognitive task period has a duration within a range of about 9 to about 11 minutes.

23. The apparatus of claim 22, wherein: said first cognitive task period has a duration of about 10 minutes; said rest period has a duration of about 5 minutes; and said second cognitive task period has a duration of 10 minutes.

24. The apparatus of claim 16, wherein the individual during said first and second cognitive task periods participate in an activity selected from the group consisting of: reading, performing math, viewing video, tracking on a computer screen, and listening.

25. The apparatus of claim 16, wherein said digitized EEG data in step (b) is obtained by utilizing a Fast Fourier Transform analysis.

26. The apparatus of claim 16, wherein said digitized EEG data in step (b) is obtained in four frequency bands: Theta (4-8 Hz), Alpha (8-14 Hz), Beta (13-22 Hz) and High Beta (22-40 Hz).

27. The apparatus of claim 16, wherein number of electrodes range from 1 to 15.

28. The apparatus of claim 16, wherein the disorders include at least one of mild cognitive impairment (MCI) in individuals with pre-dementia, dementia, dementia with Lewy bodies, Alzheimer's Disease, traumatic brain injury, Attention Deficit/Hyperactivity Disorder (ADHD), and cognitive/attentional declines associated with chronic diseases such as diabetes, cardiovascular disease, and HIV infection.

29. The apparatus of claim 16, wherein the assessment of the individual is utilized to determine the type of medication or other treatment or the amount of medication or other treatment or both the type and the amount to be prescribed to the individual for treating the disorder.

30. The apparatus of claim 16, wherein as the individuals receive a course of treatment for any of the disorders, the apparatus further comprises: repeating steps (a) through (g) at least one or more times over a select duration to determine success or efficacy of the treatment.

31. A computer program product comprising a computer readable medium having stored therein computer executable instructions for enabling at least one processor in a computer system to assess individuals for disorders associated with attentional impairments based on digitized EEG data, said digitized EEG data obtained at epochs of a plurality of frequency bands from an individual, said EEG data collected from a first cognitive task period, a rest period, and a second cognitive task period, wherein the individual performs predetermined tasks during said first and second cognitive task periods, and the individual rests during said rest period, said computer executable instructions comprising instructions for:

a) processing said EEG data to determine electrophysical power (pW) obtained from said first cognitive task period and said second cognitive task period;

b) calculating the power change distance (PCD) between said first and second cognitive task periods;

c) filtering PCD data by comparing said PCD data with a noise threshold number;

d) applying a cutoff frequency dividing said filtered PCD data into two ranges, a first range being PCD data below said cut-off frequency and a second range being PCD data above said cut-off frequency;

e) calculating a Consistency Index, said Consistency Index being defined by the absolute value of the difference between a sum of said below cut-off PCD data and a sum of said above cut off PCD data; and f) comparing said Consistency Index to a control group database to provide the assessment of the individual.

* * * * *